US011399948B2

United States Patent
Knox et al.

(10) Patent No.: US 11,399,948 B2
(45) Date of Patent: *Aug. 2, 2022

(54) STEMLESS PROSTHESIS ANCHOR COMPONENTS AND KITS

(71) Applicant: HOWMEDICA OSTEONICS CORP., Mahwah, NJ (US)

(72) Inventors: Kevin P. Knox, Fort Wayne, IN (US); Shawn M. Gargac, Fort Wayne, IN (US); Austin Wyatt Mutchler, Warsaw, IN (US); Philippe Collin, Pace (FR); George S. Athwal, London (CA)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/208,956

(22) Filed: Dec. 4, 2018

(65) Prior Publication Data

US 2019/0175354 A1 Jun. 13, 2019

Related U.S. Application Data

(60) Provisional application No. 62/597,283, filed on Dec. 11, 2017.

(51) Int. Cl.
*A61F 2/40* (2006.01)
*A61F 2/30* (2006.01)
(Continued)

(52) U.S. Cl.
CPC ........ *A61F 2/4003* (2013.01); *A61F 2/30767* (2013.01); *A61F 2/4014* (2013.01);
(Continued)

(58) Field of Classification Search
CPC ........ A61F 2/40; A61F 2/4003; A61F 2/4014; A61F 2/4081; A61F 2/4059;
(Continued)

(56) References Cited

U.S. PATENT DOCUMENTS

| 448,126 A | 3/1891 | Craig |
|---|---|---|
| 1,065,456 A | 6/1913 | Lowrey |

(Continued)

FOREIGN PATENT DOCUMENTS

| DE | 4220217 | 12/1993 |
|---|---|---|
| DE | 10233204 | 1/2004 |

(Continued)

OTHER PUBLICATIONS

Barth, et al., "Is global humeral head offset related to intramedullary canal width? A computer tomography morphometric study," Journal of Experimental Orthopaedics, 2018, vol. 5, pp. 1-8.

(Continued)

*Primary Examiner* — Marcia L Watkins
(74) *Attorney, Agent, or Firm* — Duane Morris LLP

(57) ABSTRACT

A prosthesis assembly is provided that includes a base member that has a helical structure and a cylindrical member opposite the helical structure. The cylindrical member is configured for direct connection with a reverse insert of a reverse shoulder assembly. The cylindrical member is configured for direct connection with a reverse insert spacer in some embodiments. The reverse insert can be inserted into a space defined at least in part by a wall of the cylindrical member and an inferior wall of the of the base member. The helical structure extends between a first end and a second end. The base member also can include one or more pathways. The pathway(s) is accessible from the second end and is directed toward the first end through the helical structure. The pathway is located inward of an outer periphery of the helical structure, e.g., adjacent to an inner periphery of the helical structure. The pathway extends in a space between successive portions of the helical structure. The prosthesis assembly can include a locking device that has a support member and an arm that projects away from the support (Continued)

member. The arm is configured to be disposed in the pathway when the support member is disposed adjacent to the second end of the base member. The arm is disposed through bone in the space between successive portions of the helical structure when the prosthesis assembly is implanted.

17 Claims, 30 Drawing Sheets

(51) Int. Cl.
- A61B 17/15 (2006.01)
- A61B 17/16 (2006.01)
- A61F 2/46 (2006.01)
- A61F 2/00 (2006.01)

(52) U.S. Cl.
CPC ........... A61B 17/15 (2013.01); A61B 17/1684 (2013.01); A61F 2/0077 (2013.01); A61F 2/30771 (2013.01); A61F 2/4081 (2013.01); A61F 2/4612 (2013.01); A61F 2002/305 (2013.01); A61F 2002/3085 (2013.01); A61F 2002/30224 (2013.01); A61F 2002/30289 (2013.01); A61F 2002/30354 (2013.01); A61F 2002/30357 (2013.01); A61F 2002/30476 (2013.01); A61F 2002/30484 (2013.01); A61F 2002/30594 (2013.01); A61F 2002/30599 (2013.01); A61F 2002/30604 (2013.01); A61F 2002/30607 (2013.01); A61F 2002/30616 (2013.01); A61F 2002/30632 (2013.01); A61F 2002/30667 (2013.01); A61F 2002/4018 (2013.01); A61F 2002/4022 (2013.01); A61F 2002/4074 (2013.01)

(58) Field of Classification Search
CPC .... A61F 2002/30289; A61F 2002/4011; A61F 2002/4018; A61F 2002/4022; A61F 2002/4085; A61F 2002/30291; A61F 2002/30293; A61F 2002/30294; A61F 2002/30298; A61F 2002/30632; A61F 2002/30393; A61F 2002/30395; A61F 2002/30558

See application file for complete search history.

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,623,353 A | 11/1986 | Buechel et al. |
| 4,632,111 A | 12/1986 | Roche |
| 4,662,891 A | 5/1987 | Noiles |
| 4,743,262 A | 5/1988 | Tronzo |
| 4,865,605 A | 9/1989 | Dines et al. |
| 4,883,491 A | 11/1989 | Mallory et al. |
| 4,919,670 A | 4/1990 | Dale et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,257,995 A | 11/1993 | Umber et al. |
| 5,282,865 A | 2/1994 | Dong |
| 5,358,526 A | 10/1994 | Tornier |
| 5,489,309 A | 2/1996 | Lackey et al. |
| 5,489,310 A | 2/1996 | Mikhail |
| 5,507,817 A | 4/1996 | Craig et al. |
| 5,540,697 A | 7/1996 | Rehmann et al. |
| 5,681,134 A | 10/1997 | Ebert |
| 5,702,486 A | 12/1997 | Craig et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,954,727 A | 9/1999 | Collazo |
| 5,976,148 A | 11/1999 | Charpenet et al. |
| 6,045,582 A | 4/2000 | Prybyla |
| 6,063,124 A | 5/2000 | Amstutz |
| 6,099,214 A | 8/2000 | Lee et al. |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Okun et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,666,874 B2 | 12/2003 | Heitzmann et al. |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,208,222 B2 | 4/2007 | Rolfe et al. |
| 7,344,565 B2 | 3/2008 | Seyer et al. |
| 7,465,319 B2 | 12/2008 | Tornier |
| 7,476,228 B2 | 1/2009 | Abou |
| 7,476,253 B1 | 1/2009 | Craig et al. |
| 7,585,327 B2 | 9/2009 | Winslow |
| 7,615,080 B2 | 11/2009 | Ondrla |
| 7,637,703 B2 | 12/2009 | Khangar et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,758,650 B2 | 7/2010 | Dews et al. |
| 7,887,544 B2 | 2/2011 | Tornier et al. |
| 7,927,376 B2 | 4/2011 | Leisinger et al. |
| D643,926 S | 8/2011 | Collins |
| 8,021,370 B2 | 9/2011 | Fenton et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |

(56) References Cited

U.S. PATENT DOCUMENTS

| | | |
|---|---|---|
| 8,202,275 B2 | 6/2012 | Wozencroft |
| 8,221,037 B2 | 7/2012 | Neitzell |
| 8,231,682 B2 | 7/2012 | LaFosse |
| 8,246,687 B2 | 8/2012 | Katrana et al. |
| 8,277,512 B2 | 10/2012 | Parrott et al. |
| 8,317,871 B2 | 11/2012 | Stone et al. |
| 8,409,798 B2 | 4/2013 | Luy et al. |
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| 8,591,592 B2 | 11/2013 | Dreyfuss |
| 8,641,773 B2 | 2/2014 | Bergin et al. |
| 8,647,387 B2 | 2/2014 | Winslow |
| 8,663,334 B2 | 3/2014 | Viscardi et al. |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,795,379 B2 | 8/2014 | Smith et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| 8,992,623 B2 | 3/2015 | Hopkins et al. |
| D745,678 S | 12/2015 | Courtney et al. |
| 9,233,003 B2 | 1/2016 | Roche et al. |
| 9,289,218 B2 | 3/2016 | Courtney, Jr. et al. |
| 9,326,865 B2 | 5/2016 | Katrana et al. |
| 9,364,334 B2 | 6/2016 | Katrana et al. |
| 9,498,345 B2 | 11/2016 | Burkhead, Jr. et al. |
| 9,510,839 B2 | 12/2016 | Maroney et al. |
| 9,603,712 B2 | 3/2017 | Bachmaier |
| 9,615,928 B2 | 4/2017 | Visser et al. |
| 9,820,859 B2 | 11/2017 | Gervasi et al. |
| 10,166,032 B2 | 1/2019 | Stone et al. |
| D840,539 S | 2/2019 | Courtney et al. |
| 10,335,285 B2 | 7/2019 | Viscardi et al. |
| 10,368,999 B2 | 8/2019 | Greiwe |
| 10,433,969 B2 | 10/2019 | Humphrey |
| 10,456,264 B2 | 10/2019 | Hodorek et al. |
| 10,463,499 B2 | 11/2019 | Emerick et al. |
| 11,229,524 B2 | 1/2022 | Sperling |
| 2001/0034553 A1* | 10/2001 | Michelson ............ A61F 2/446 623/17.11 |
| 2001/0047210 A1 | 11/2001 | Wolf |
| 2002/0116007 A1 | 8/2002 | Lewis |
| 2002/0156534 A1 | 10/2002 | Grusin et al. |
| 2003/0028253 A1 | 2/2003 | Stone et al. |
| 2003/0031521 A1 | 2/2003 | Haughton et al. |
| 2003/0114933 A1 | 6/2003 | Bouttens et al. |
| 2003/0125810 A1 | 7/2003 | Sullivan et al. |
| 2004/0049270 A1 | 3/2004 | Gewirtz |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0243136 A1 | 12/2004 | Gupta et al. |
| 2004/0254646 A1 | 12/2004 | Stone et al. |
| 2005/0107882 A1 | 5/2005 | Stone et al. |
| 2005/0112397 A1 | 5/2005 | Rolfe et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0020344 A1 | 1/2006 | Shultz et al. |
| 2006/0064173 A1 | 3/2006 | Guederian |
| 2006/0089656 A1 | 4/2006 | Allard et al. |
| 2006/0142866 A1 | 6/2006 | Baratz et al. |
| 2006/0195105 A1 | 8/2006 | Teeny et al. |
| 2006/0200165 A1 | 9/2006 | Tulkis |
| 2006/0200249 A1 | 9/2006 | Beguin et al. |
| 2007/0010825 A1 | 1/2007 | Leisinger et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162141 A1 | 7/2007 | Dews et al. |
| 2007/0173945 A1 | 7/2007 | Wiley et al. |
| 2007/0212179 A1 | 9/2007 | Khangar et al. |
| 2007/0219562 A1 | 9/2007 | Slone et al. |
| 2007/0225817 A1 | 9/2007 | Reubelt et al. |
| 2007/0233132 A1 | 10/2007 | Valla |
| 2008/0021564 A1 | 1/2008 | Gunther |
| 2008/0077146 A1 | 3/2008 | Pernsteiner et al. |
| 2008/0195111 A1 | 8/2008 | Anderson |
| 2008/0249577 A1 | 10/2008 | Dreyfuss |
| 2009/0171462 A1 | 7/2009 | Poncet et al. |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0087927 A1 | 4/2010 | Roche et al. |
| 2010/0114326 A1 | 5/2010 | Winslow et al. |
| 2010/0191340 A1 | 7/2010 | Dreyfuss |
| 2010/0274360 A1 | 10/2010 | Gunther |
| 2010/0278601 A1 | 11/2010 | Beynon |
| 2011/0153023 A1 | 6/2011 | Deffenbaugh et al. |
| 2011/0224673 A1 | 9/2011 | Smith |
| 2011/0276144 A1 | 11/2011 | Wirth et al. |
| 2011/0313533 A1 | 12/2011 | Gunther |
| 2012/0022664 A1 | 1/2012 | Vandermeulen et al. |
| 2012/0109321 A1 | 5/2012 | Stone et al. |
| 2012/0184964 A1 | 7/2012 | Hudak, Jr. |
| 2012/0221111 A1 | 8/2012 | Burkhead, Jr. et al. |
| 2012/0253467 A1 | 10/2012 | Frankle |
| 2012/0265315 A1 | 10/2012 | Kusogullari et al. |
| 2012/0277880 A1 | 11/2012 | Winslow et al. |
| 2012/0296435 A1 | 11/2012 | Ambacher |
| 2013/0018476 A1 | 1/2013 | Katrana et al. |
| 2013/0123929 A1 | 5/2013 | McDaniel et al. |
| 2013/0123930 A1 | 5/2013 | Burt |
| 2013/0150972 A1 | 6/2013 | Iannotti et al. |
| 2013/0173006 A1 | 7/2013 | Duport |
| 2013/0178943 A1 | 7/2013 | Duport |
| 2013/0190882 A1 | 7/2013 | Humphrey |
| 2013/0211539 A1 | 8/2013 | McDaniel et al. |
| 2013/0261626 A1 | 10/2013 | Chavarria et al. |
| 2013/0261629 A1 | 10/2013 | Anthony et al. |
| 2013/0261754 A1 | 10/2013 | Anthony et al. |
| 2013/0282129 A1 | 10/2013 | Phipps |
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0074246 A1 | 3/2014 | Huebner et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257499 A1 | 9/2014 | Winslow et al. |
| 2014/0296988 A1 | 10/2014 | Winslow et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0134066 A1 | 5/2015 | Bachmaier |
| 2015/0250472 A1 | 9/2015 | Ek et al. |
| 2015/0250601 A1 | 9/2015 | Humphrey |
| 2015/0289984 A1 | 10/2015 | Budge |
| 2015/0297354 A1 | 10/2015 | Walch et al. |
| 2015/0305877 A1 | 10/2015 | Gargac et al. |
| 2016/0051367 A1 | 2/2016 | Gervasi et al. |
| 2016/0157911 A1 | 6/2016 | Courtney, Jr. et al. |
| 2016/0324648 A1* | 11/2016 | Hodorek ............... A61F 2/4014 |
| 2017/0105843 A1 | 4/2017 | Britton et al. |
| 2017/0273800 A1* | 9/2017 | Emerick ............... A61F 2/4014 |
| 2017/0304063 A1 | 10/2017 | Hatzidakis et al. |
| 2017/0367836 A1 | 12/2017 | Cardon et al. |
| 2018/0092760 A1 | 4/2018 | Sperling et al. |
| 2018/0271667 A1 | 9/2018 | Kemp et al. |
| 2018/0325687 A1 | 11/2018 | Deransart et al. |
| 2019/0105165 A1 | 4/2019 | Sikora et al. |

(56) References Cited

U.S. PATENT DOCUMENTS

| | | |
|---|---|---|
| 2019/0105167 A1 | 4/2019 | Hatzidakis et al. |
| 2019/0105169 A1 | 4/2019 | Sperling |
| 2019/0159906 A1 | 5/2019 | Knox et al. |
| 2019/0216518 A1 | 7/2019 | Courtney, Jr. et al. |
| 2019/0328536 A1 | 10/2019 | Martin et al. |
| 2020/0008947 A1 | 1/2020 | Emerick et al. |
| 2020/0121467 A1 | 4/2020 | Hodorek et al. |
| 2020/0146834 A1 | 5/2020 | Hodorek et al. |
| 2020/0214845 A1 | 7/2020 | Knox et al. |

FOREIGN PATENT DOCUMENTS

| | | |
|---|---|---|
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 952 788 | 8/2008 |
| EP | 1 867 303 | 9/2010 |
| EP | 1 977 720 | 1/2011 |
| EP | 1 550 420 | 2/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2586387 A1 | 5/2013 |
| EP | 2 616 013 | 7/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 8/2015 |
| EP | 2 353 549 | 6/2016 |
| EP | 3 117 801 | 1/2017 |
| EP | 2 965 720 B1 | 7/2017 |
| EP | 3 539 513 | 9/2019 |
| FR | 2 674 122 | 9/1992 |
| FR | 2997290 B1 | 11/2015 |
| GB | 2405346 | 3/2005 |
| JP | 2009523578 A | 6/2009 |
| WO | WO 01/67988 | 9/2001 |
| WO | WO 02/17822 | 3/2002 |
| WO | WO 2008/011078 | 1/2008 |
| WO | WO 2008/146124 | 12/2008 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |
| WO | WO 2014/058314 | 4/2014 |
| WO | WO 2015/112307 | 7/2015 |
| WO | 2016094739 A1 | 6/2016 |
| WO | WO 2016/094739 | 6/2016 |
| WO | WO 2017/165090 | 9/2017 |
| WO | WO 2017/184792 | 10/2017 |
| WO | WO 2018/022227 | 2/2018 |
| WO | WO 2019/060780 | 3/2019 |
| WO | WO 2019/106278 | 6/2019 |
| WO | WO 2020/072452 | 4/2020 |
| WO | WO 2020/072454 | 4/2020 |

OTHER PUBLICATIONS

Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.

Routman, et al., "Reverse Shoulder Arthroplasty Prosthesis Design Classification System," Bulletin of the Hospital for Joint Diseases, 2015, vol. 73 (Suppl 1), pp. S5-S14.

Non-Final Office Action issued in connection with U.S. Appl. No. 16/648,128, dated Mar. 28, 2022, 15 pages.

Non-Final Office Action issued in connection with U.S. Appl. No. 17/250,964, dated Jul. 26, 2021, 27 pages.

Final Rejection issued in connection with U.S. Appl. No. 16/249,720, dated Aug. 20, 2021, 40 pages.

Final Rejection issued in connection with U.S. Appl. No. 16/580,367, dated Aug. 24, 2021, 9 pages.

Final Rejection issued in connection with U.S. Appl. No. 17/250,964, dated Sep. 9, 2021, 22 pages.

Non-Final Office Action issued in connection with U.S. Appl. No. 16/519,937, dated Aug. 17, 2021, 21 pages.

Non-Final Office Action issued in connection with U.S. Appl. No. 17/250,964, dated Feb. 24, 2022, 12 pages.

First Office Action issued in connection with Japanese Patent Application No. 2019-555151, dated Feb. 21, 2022, 5 pages.

Third Examination Report issued in connection with Australian Patent Application No. 2019355854, dated May 10, 2022, 4 pages.

First Examination Report issued in connection with Australian Patent Application No. 2021250994, dated Jun. 2, 2022, 5 pages.

* cited by examiner

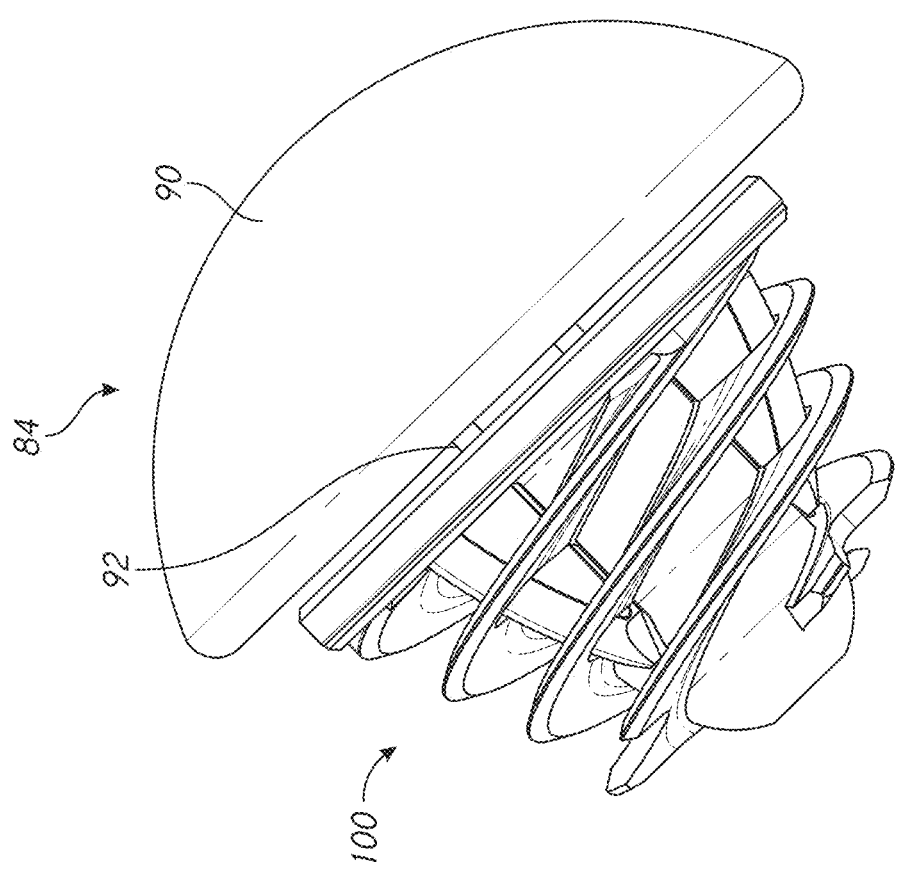

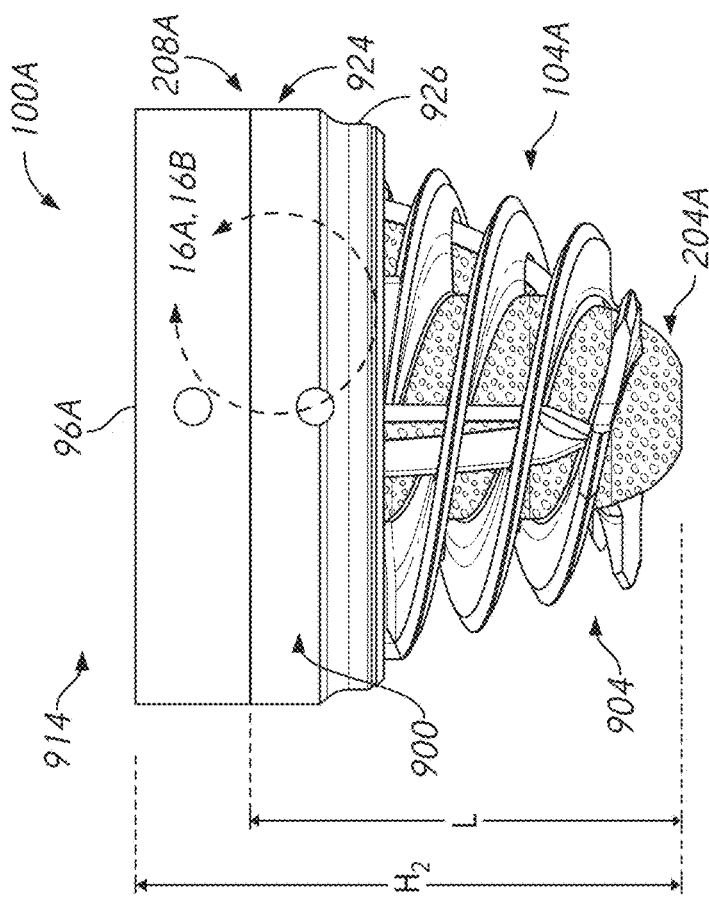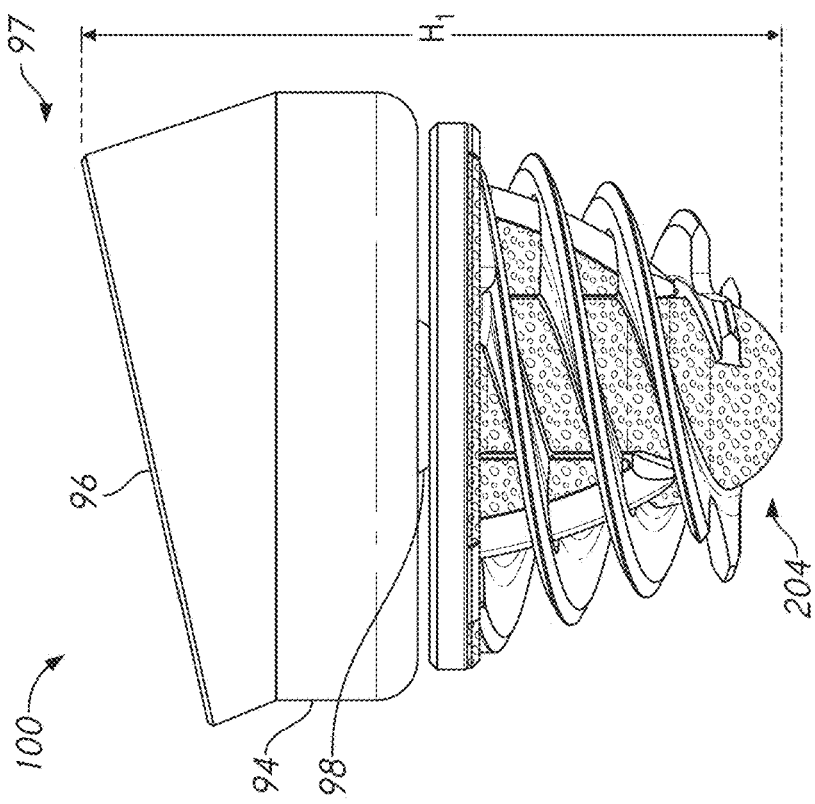
FIG. 18A
FIG. 18B

STEMLESS PROSTHESIS ANCHOR COMPONENTS AND KITS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present disclosure relates to a stemless prosthesis anchor component of a joint prosthesis that can be coupled with a concave articular body such as is used in reverse shoulder arthroplasty.

Description of the Related Art

Skeletal joints have a variety of configurations providing for a wide range of smooth movement of two or more bones relative to each other. For example, in a shoulder joint, the head of the humerus interacts with the glenoid cavity of the scapula in a manner similar to a "ball and socket" joint. Over time, it may become necessary to replace a joint, such as the shoulder joint, with a prosthetic joint. The prosthetic joint can include components mounted to one, two or more than two bones at the joint. For example, the prosthetic joint can include a humeral component, a glenoid component or both a humeral and a glenoid component.

Conventional humeral components include a humeral head coupled with a stemless humeral anchor to minimize bone loss and other disadvantages of the use of humeral anchors with stems. Stemless humeral anchors can be coupled with anatomic articular bodies and with reverse articular bodies. An anatomic articular body has a convex articular surface that faces the glenoid portion of the joint. A reverse articular body has a concave articular surface that faces the glenoid portion.

Reverse articular bodies conventionally are connected to an intermediate component that is connected to a stemless humeral anchor. This intermediate component, which is sometimes called a tray, adds thickness to the assembly and can therefore limit how close the humerus can be placed to the glenoid following a reverse shoulder implant procedure. While a stemless humeral anchor could be inset into the epiphysis of the humerus inferior of the resection plane to provide a larger range of the position of the humerus to the glenoid, inset positioning can compromise the integrity of the fixation into the humerus.

SUMMARY OF THE INVENTION

Accordingly, there is a need for additional stemless shoulder assemblies that enhances a surgeon's ability to position the humerus relative to the scapula following implantation of stemless humeral anchors. A wider range of possible positions can allow for better soft tissue tensioning which can help to reduce, e.g., minimize, a risk of dislocation of the shoulder joint or acromion fractures. Such assemblies preferably include components designed to preserve bone in initial implantation while enhancing initial pull-out and back-out resistance. Preferably enhanced initial dislodgement resistance will also provide excellent long term fixation.

In one embodiment, a shoulder assembly is provided that includes a base member and a locking device. The base member includes a collar, a helical structure, and a first pathway projecting distally of the collar. The helical structure extends from the collar in a distal direction. The first pathway projects distally of the collar and through the helical structure. The first pathway is disposed adjacent to an inner periphery of the helical structure. The first pathway is generally transverse to the helical structure and extending in a space between successive portions of the helical structure. The locking device has a proximal support and a first arm that projects distally of the proximal support. The first arm is configured to be disposed in the first pathway that projects distally of the collar when the proximal support is disposed adjacent to the collar. The first arm is disposed through bone in the space between successive portions of the helical structure when the shoulder assembly is implanted. A cylindrical member is disposed in some embodiment on an end of the base opposite the helical structure, e.g., away from the collar. The cylindrical member configured to directly engage a reverse shoulder insert.

In some embodiments, a kit can be provided that includes a shoulder assembly as described above, an anatomic articular component, and a reverse articular component. The anatomic articular component is mateable with the shoulder assembly. The anatomic articular component has a convex articular surface adapted to articulate with a concave surface of or on a scapula of a patient. The reverse articular component is mateable with the shoulder assembly. The reverse articular component comprises a concave articular surface adapted to articulate with a convex surface on a scapula of a patient. The reverse articular component includes a retention portion for mating the reverse articular component directly to the base member, e.g., at a cylindrical portion thereof.

In another embodiment, a prosthesis assembly is provided that includes a base member that has a helical structure and a first pathway. The base member has a first end and a second end. The helical structure extends between the first end and the second end. The first end comprises a distal or medial end in some applications. The second end comprises a proximal end or a lateral end in some applications. The first pathway is accessible from the second end and is directed toward the first end through the helical structure. The first pathway is located inward of an outer periphery of the helical structure, e.g., adjacent to an inner periphery of the helical structure. The first pathway is generally transverse to the helical structure. The first pathway extends in a space between successive portions of the helical structure. The prosthesis assembly includes a locking device that has a support member and a first arm that projects away from the support member. The first arm is configured to be disposed in the first pathway when the support member is disposed adjacent to the second end of the base member. The first arm is disposed through bone in the space between successive portions of the helical structure when the prosthesis assembly is implanted. The prosthesis assembly can be configured such that the locking device engages with the base member with a first side disposed adjacent to the base member and a second portion disposed adjacent to a reverse articular component engaged with the base member.

The prosthesis assemblies discussed herein can be mated with a proximal humerus. The prosthesis assemblies discussed herein can be mated with other anatomy as well, such as a glenoid of a scapula. The prosthesis assemblies discussed herein can be mated with a bone adjacent to an elbow joint, such as a distal humerus or a proximal radius. The prosthesis assemblies discussed herein can be mated with a bone adjacent to a wrist joint, such as a distal radius. The prosthesis assemblies discussed herein can be mated with a bone adjacent to the hip, such as a proximal femur. The prosthesis assemblies discussed herein can be mated with a bone adjacent to a knee joint, such as a distal femur or a proximal tibia. The prosthesis assemblies discussed herein can be mated with a bone adjacent to an ankle joint, such as a distal tibia or a proximal talus. The description of the uses of the assemblies disclosed herein in connection with these and other bones is supplemented by reference to US application no. PCT/US2017/038843, which is hereby incorporated herein by reference.

In another embodiment, a method of implanting a prosthesis is provided. The method includes advancing by rotation a base member into a bone adjacent to a joint. The bone can include an epiphysis of a humerus of a patient. The bone can include a glenoid of a scapula of a patient. The bone can include a distal portion of a humerus adjacent to an elbow joint. The bone can include a proximal portion of a radius adjacent to an elbow joint. The bone can include a distal portion of a radius adjacent to a wrist joint. The bone can include a proximal portion of a femur adjacent to a hip joint. The bone can include a distal portion of a femur adjacent to a knee joint. The bone can include a proximal portion of a tibia adjacent to a knee joint. The bone can include a distal portion of a tibia adjacent to an ankle joint. The bone can include a proximal portion of a talus adjacent to an ankle joint. The base member comprising a helical structure configured to engage cancellous bone of the epiphysis or other portion of any of the bones set forth above. The helical structure can be disposed about a submergible portion that, in use, is submerged into the cancellous bone inferior of a resection plane of the epiphysis. An external surface disposed superior to the submergible portion can have a bone interface portion advanced into engagement with an exposed face of the humerus. An exposed portion of the base member can be disposed superior to the bone interface portion. A locking device is advanced by linear translation into the base member. The locking device can be inserted into a cylindrical member disposed at the exposed portion of the base member. An opening into the cylindrical member can comprise a superior end of the exposed portion of the base member. The locking device has at least one arm adapted to span a gap between adjacent portions of the helical structure. The locking device contacts the cancellous bone in the gap. A reverse articular component can be selected for a patient and can be inserted into direct engagement with the concave member of the base member.

In another embodiment, a shoulder assembly is provided that includes a base member and a reverse insert. The base member has a submergible portion, an exposed portion, and a cylindrical member extending along the submergible portion. The submergible portion has a helical structure. The cylindrical member extends from the submergible portion to the exposed portion. The reverse insert has an articular portion and a retention portion. The articular portion includes a concave surface configured to articulate over a glenosphere. The (99). The cylindrical member and the retention portion are configured to provide for direct coupling between the reverse insert and the base member.

In another embodiment a prosthesis assembly is provided that includes a base member and a locking device. The base member has a first end and a second end. The base member has a cylindrical member that is configured to receive and directly couple with a reverse insert. The base member has a helical structure that extends between the first end and the second end. The base member has a first pathway that is accessible from the second end and that is directed toward the first end through the helical structure. The first pathway is located adjacent to an inner periphery of the helical structure. The first pathway is generally transverse to the helical structure and extends in a space between successive portions of the helical structure. The locking device has a support member and a first arm projecting away from the support member. The first arm is configured to be disposed in the first pathway when the support member is disposed adjacent to the second end of the base member. The first arm is disposed through bone in the space between successive portions of the helical structure when the prosthesis assembly is implanted.

In another embodiment a method of implanting a prosthesis is provided in which a base member that has a cylindrical member is advanced by rotation into a humerus of a patient such that a helical structure of the base member is submerged in and engages cancellous bone of and does not extend distally of an epiphysis of the humerus. The cylindrical member is accessible at a resection face of the humerus when the base member is so advanced. A locking device is advanced into the base member until at least one elongate member spans a space between adjacent portions of the helical structure to contact the cancellous bone in the space. A retention portion of a reverse articular insert is inserted into the cylindrical member of the base member to directly connect the reverse articular insert with the cylindrical member of the base member.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 17 is a side view of the stemless shoulder assembly of FIG. 2 coupled with an anatomic articular component of the kit illustrated in FIG. 1;

FIG. 18A is a side view of the stemless shoulder assembly of FIG. 2 coupled with a reverse articular component of the kit illustrated in FIG. 1;

FIG. 18B is a side view of the stemless shoulder assembly assembled from the kit of FIG. 1C with a reverse articular component coupled directly with a stemless anchor;

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1:
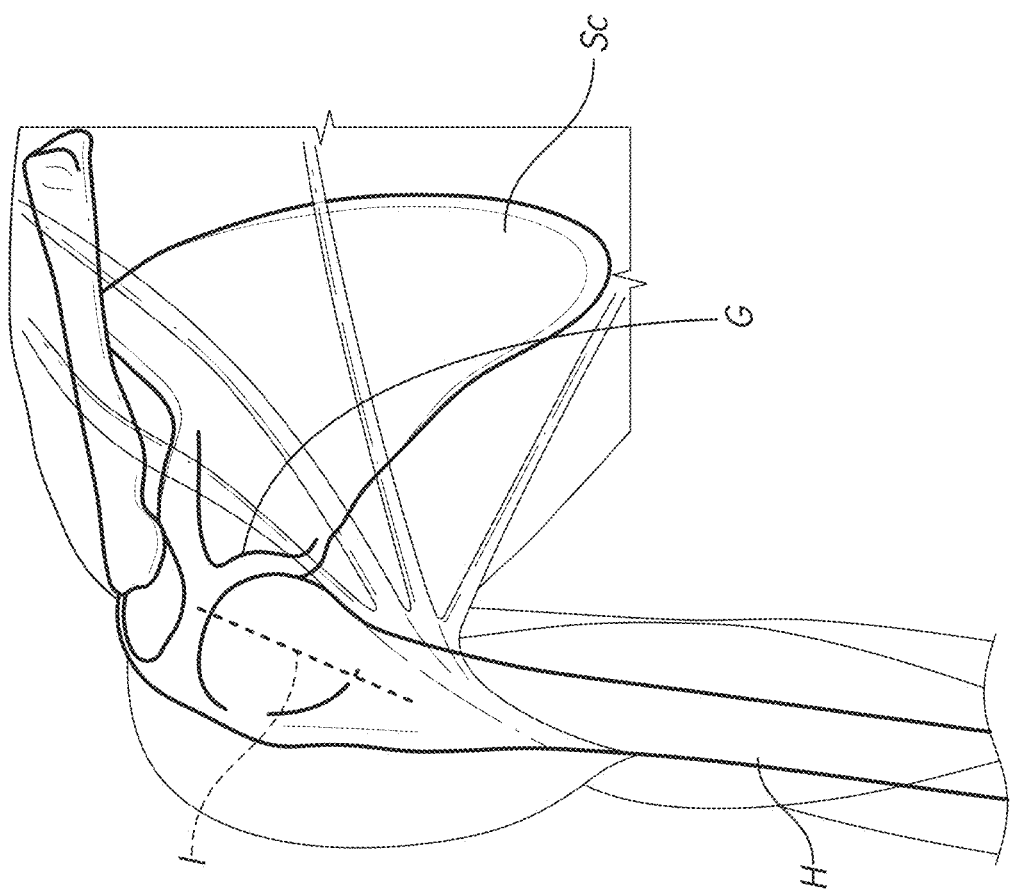
FIG. 1 is a schematic view of a glenohumeral (shoulder) joint during an early stage of a shoulder surgery.
Figure 1A:
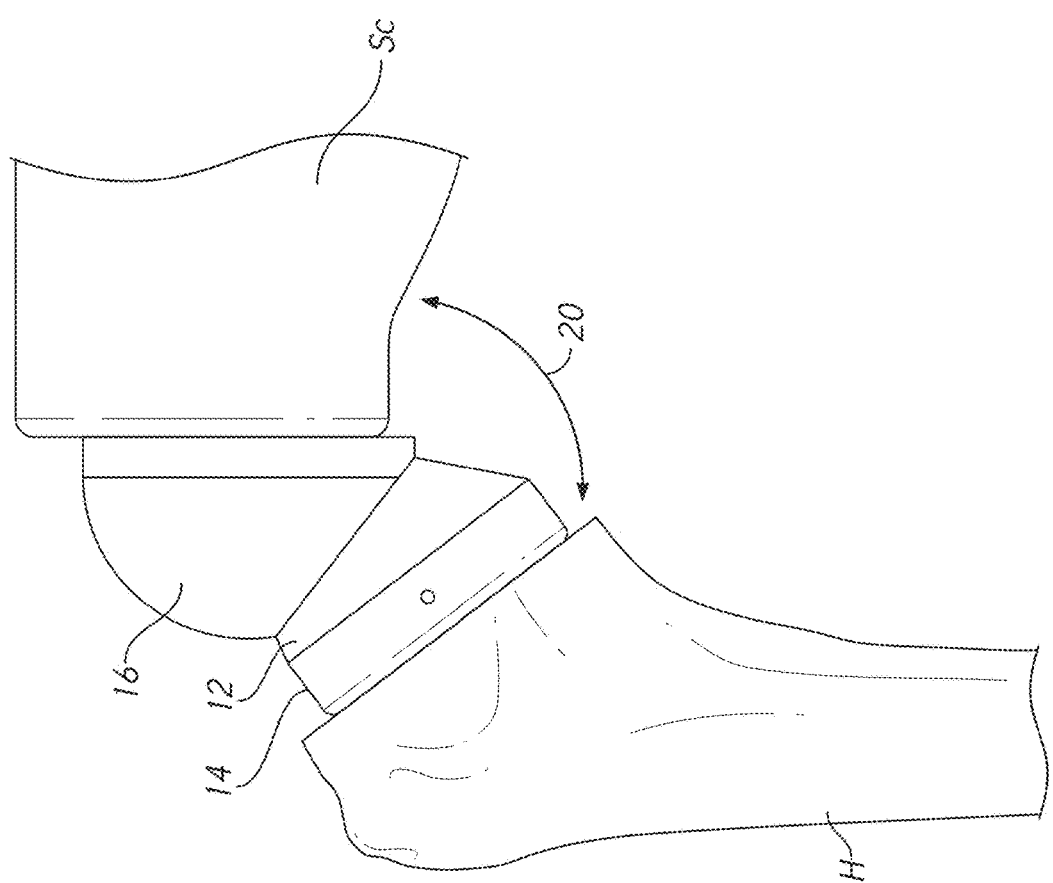
FIG. 1A is a schematic view of reverse shoulder assembly placed in a shoulder joint.

This application is directed to shoulder implants that provide greater control of the soft tissue tension around the joint following implantation. The improvements herein enable a patient to have an appropriate level of tension in the soft tissue to provide good range of motion while reducing the risk of dislocation of the shoulder joint or acromion fracture following surgery. FIG. 1 illustrates a shoulder joint that includes a humerus H and a glenoid G of a scapula Sc. Soft tissue around the joint is shown schematically as well. In an early part of a procedure for repairing the shoulder joint an incision I is made in the soft tissue. The incision I provides access to the head of the humerus H and the glenoid G. Greater access is often provided by dislocating the natural joint. Typically the humerus H is resected to remove the natural articular component of the humerus H. FIG. 1A shows the humerus H resected and a conventional reverse shoulder joint assembly implanted in the humerus H and the glenoid G. Specifically, an anchor is inserted into the resected humerus H and a concave articular component 12 is mounted to the anchor. The anchor would be located in the humerus H in FIG. 1A and thus not visible but could be a conventional stemmed anchor. The concave articular component 12 is indirectly mounted to the anchor 10 by an intervening tray 14. The motion of the prosthetic shoulder joint is provided between the concave articular component 12 and a glenosphere 16 that is mounted to the glenoid G. The prosthesis illustrated in FIG. 1A is a reverse shoulder prosthesis because in the natural shoulder joint the glenoid G has a concave shape and the head of the humerus H has a convex shape.

The arrow 20 in FIG. 1A illustrates an aspect of the range of motion of the humerus H relative to the scapula Sc. This motion and a risk of dislocation following surgery are a function of how much tension is placed on the soft tissue around the humerus H and the scapula Sc which is related to the location of the center of the concave articular component 12. The location of the center of the concave articular component 12 is adjustable over a range. However, one limit on the ability to adjust soft tissue tensioning is the minimum height of the concave articular component from the resection surface of the humerus H. The minimum dimension could be less, providing a greater range of adjustment of the soft tissue tensioning if the tray 14 could be eliminated or the height of the concave articular component 12 from the resection plane otherwise reduced.

Figure 1B:
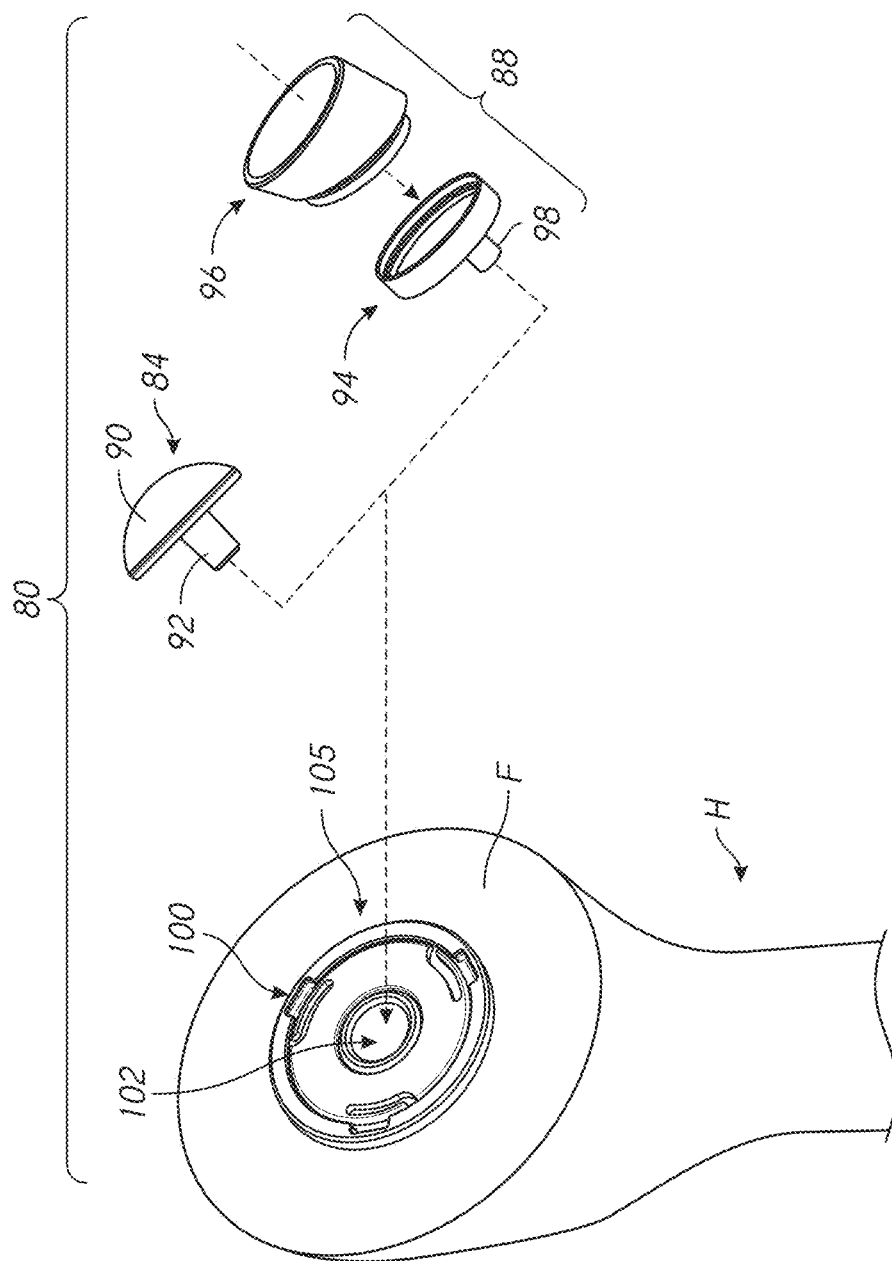
FIG. 1B is a perspective view of one embodiment of a stemless shoulder assembly shown mounted in a humerus, and further illustrates a kit including anatomic and reverse shoulder articular components.

FIG. 1B shows an embodiment of a shoulder arthroplasty kit 80 that includes a shoulder assembly 100. The kit 80 can be combined with a shoulder arthroplasty kit 80A discussed below. The kit 80 is configured for allowing a surgeon to provide an anatomic arrangement or a reverse arrangement. The kit 80A can be used if during the procedure (or before) the patient is deemed to benefit from an initial reverse procedure. The kits 80, 80A can be packaged together or separately.

Figure 1C:
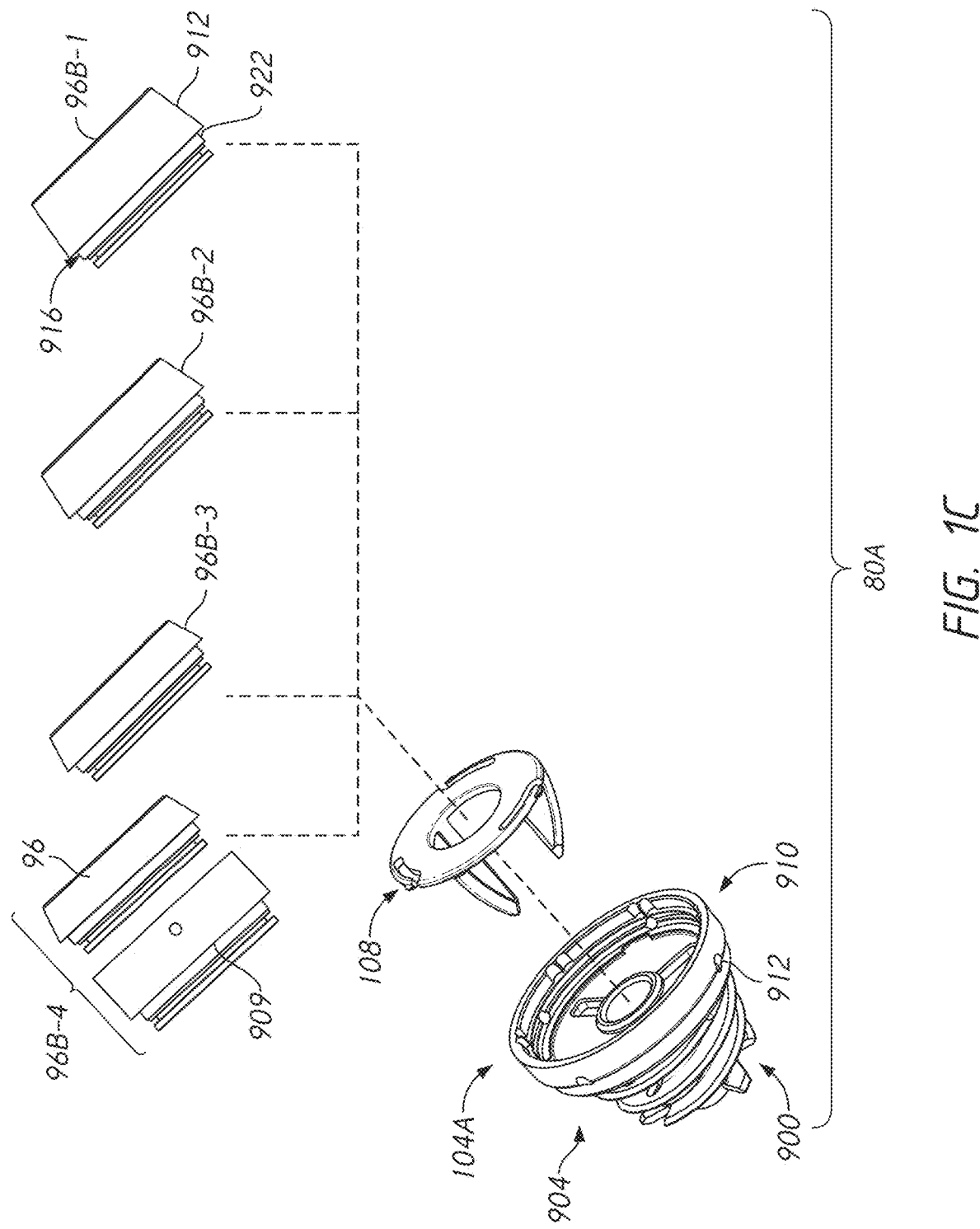
FIG. 1C is a perspective view of one embodiment of a stemless shoulder assembly shown mounted in a humerus, and further illustrating a kit including reverse shoulder articular components.
Figure 18:
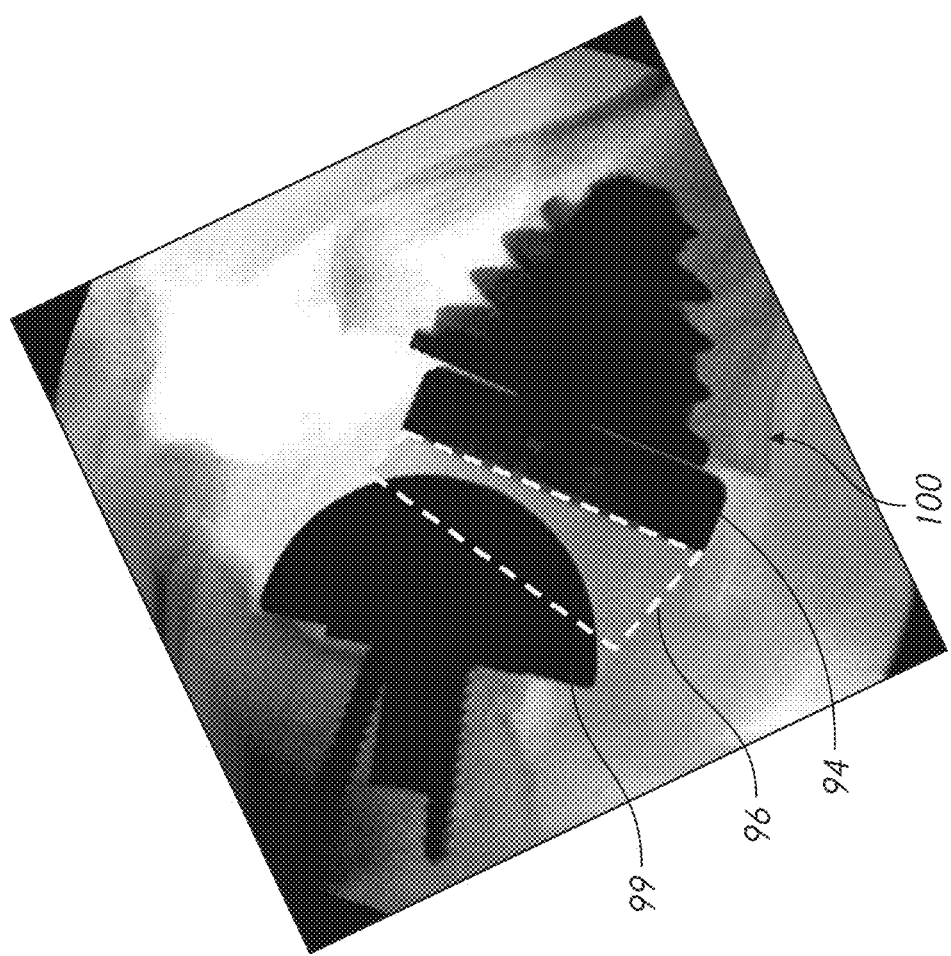
FIG. 18 shows a reverse shoulder prosthesis including a reverse articular component coupled with the humerus and a convex glenoid component, sometimes referred to as a glenoid sphere, coupled with the scapula.

The kit 80 can include one or both of an anatomic articular component 84 and a reverse articular component 88. The anatomic articular component 84 can comprise a one-piece structure including a convex articular surface 90 disposed on a proximal or lateral side and a tapered projection 92 disposed on a distal side thereof. The reverse articular component 88 can comprise a two-piece structure including a tray 94 and an insert 96. In other embodiments, the articular component 88 has a one-piece configuration. In other embodiments, the articular component 88 has a monolithic configuration. Monolithic embodiments can comprise a one material configuration. Monolithic embodiments can comprise two or more material. The insert 96 can mate with the tray 94 in any suitable manner, such as by interference fit or snap fit. The tray 94 can include a tapered projection 98. In other embodiments the tray 94 can be eliminated such that the insert 96 can mate directly with a shoulder assembly 100A discussed below. FIGS. 17 and 18 show a glenoid sphere 99 that can be included in some embodiments of the kit 80. Such a variation of the kit 80 also can include corresponding components for anchoring the glenoid sphere 99 in or to a glenoid. The insert 96 is shown in just one embodiment in which the insert 96 is angled, such that a plane intersecting the medial side of the insert 96 is at an angle to the side that faces the shoulder assembly 100 providing a thicker superior portion. In other embodiments the insert 96 is angled, such that a plane intersecting the medial side of the insert 96 is at an angle to the side that faces the shoulder assembly 100 providing a thicker inferior portion. In other embodiments the insert 96 is not angled, such that the plane intersecting the medial side of the insert 96 is substantially parallel to the side that faces the shoulder assembly 100 as shown in the kits of FIGS. 1C and 1n the combinations of FIGS. 2A and 18C and the assembly of FIG. 18B.

Figure 19A:
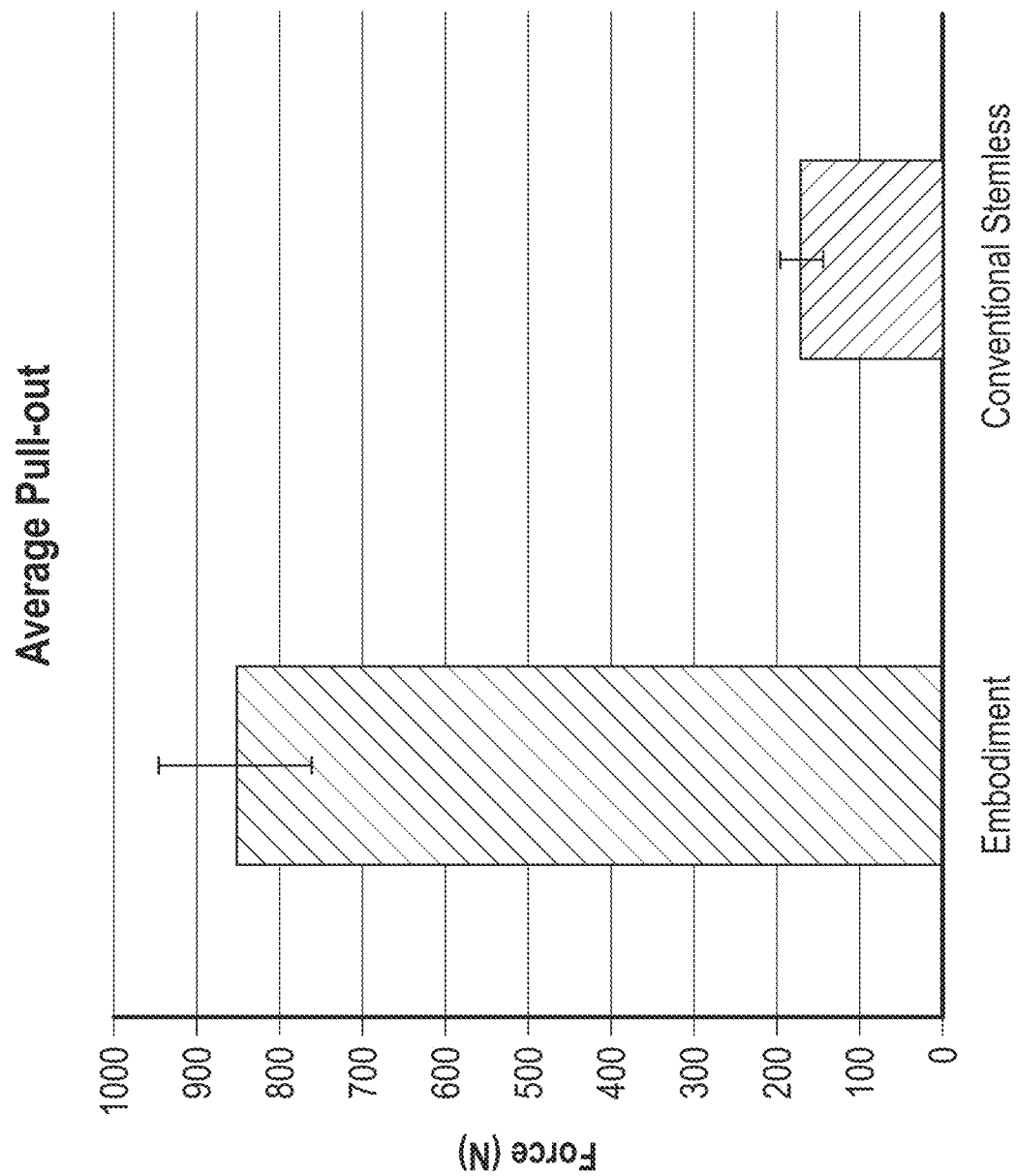
FIGS. 19A and 19B show comparative pull out and lever out performance of an embodiment as disclosed herein compared to a conventional stemless implant.
Figure 19B:
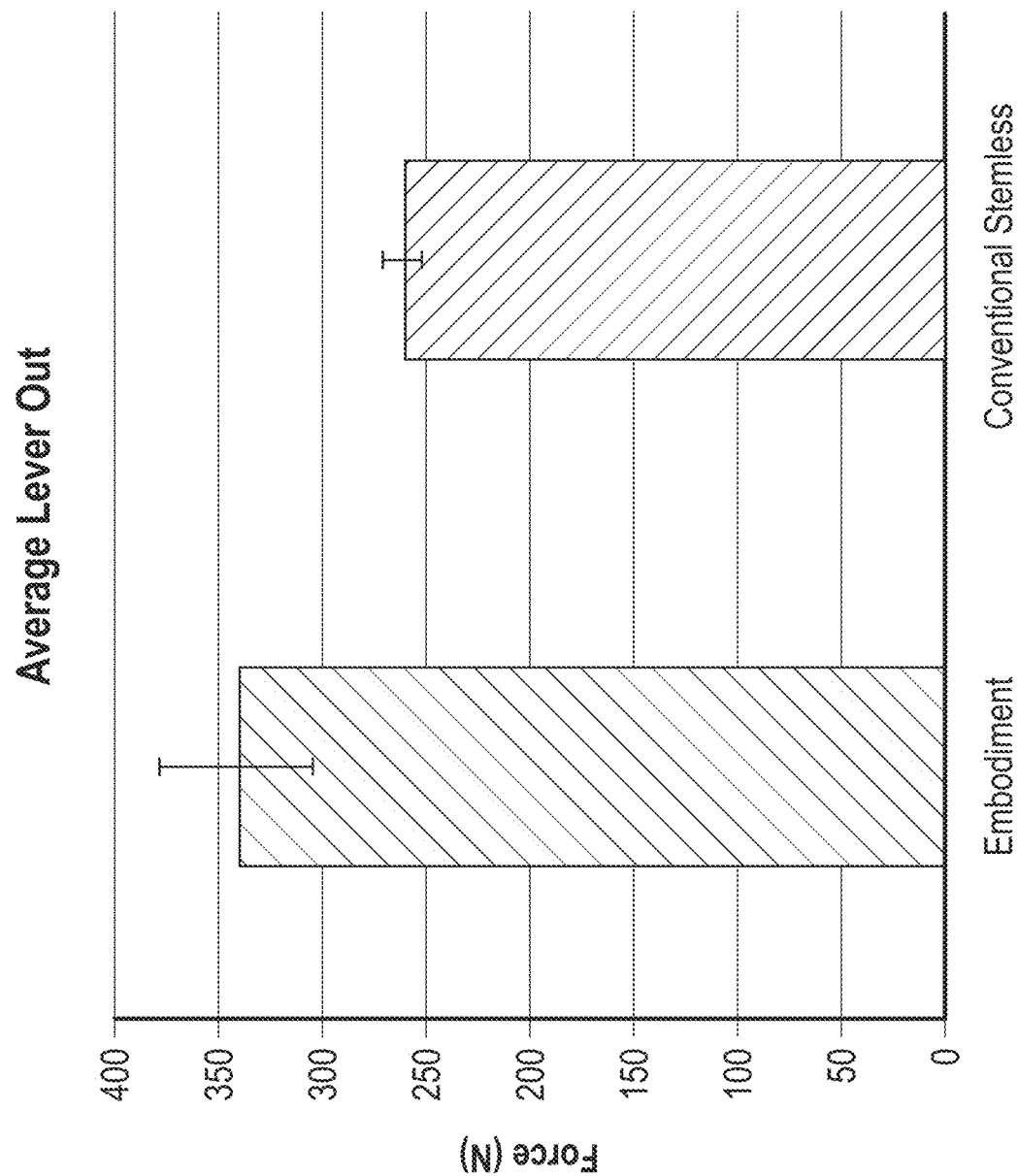

FIG. 1B shows the shoulder assembly 100, as further described below in connection with FIGS. 2-7, implanted in an exposed face F of a humerus H. The assembly 100 has a recess 102 in which further components of a prosthetic shoulder joint can be secured. The assembly 100 and the recess 102 enable the humerus H to be fitted with either an anatomical shoulder by receiving the anatomic articular component 84, more particularly, the projection 92 or a reverse shoulder component 88 by receiving the projection 98 either initially or as part of a revision procedure. Methods of using the kit 80 to implant the shoulder assembly 100 as part of a shoulder prosthesis are discussed below in connection with FIGS. 8-16. FIGS. 19A and 19B illustrate the performance of certain embodiments compared to a prior art design. While incremental differences in these embodiments and methods are discussed below, it is to be understood that features of each embodiment can be combined with features of the other embodiments, as appropriate.

I. Humeral Shoulder Assemblies Having Rotation Control Locking Devices

Figure 7:
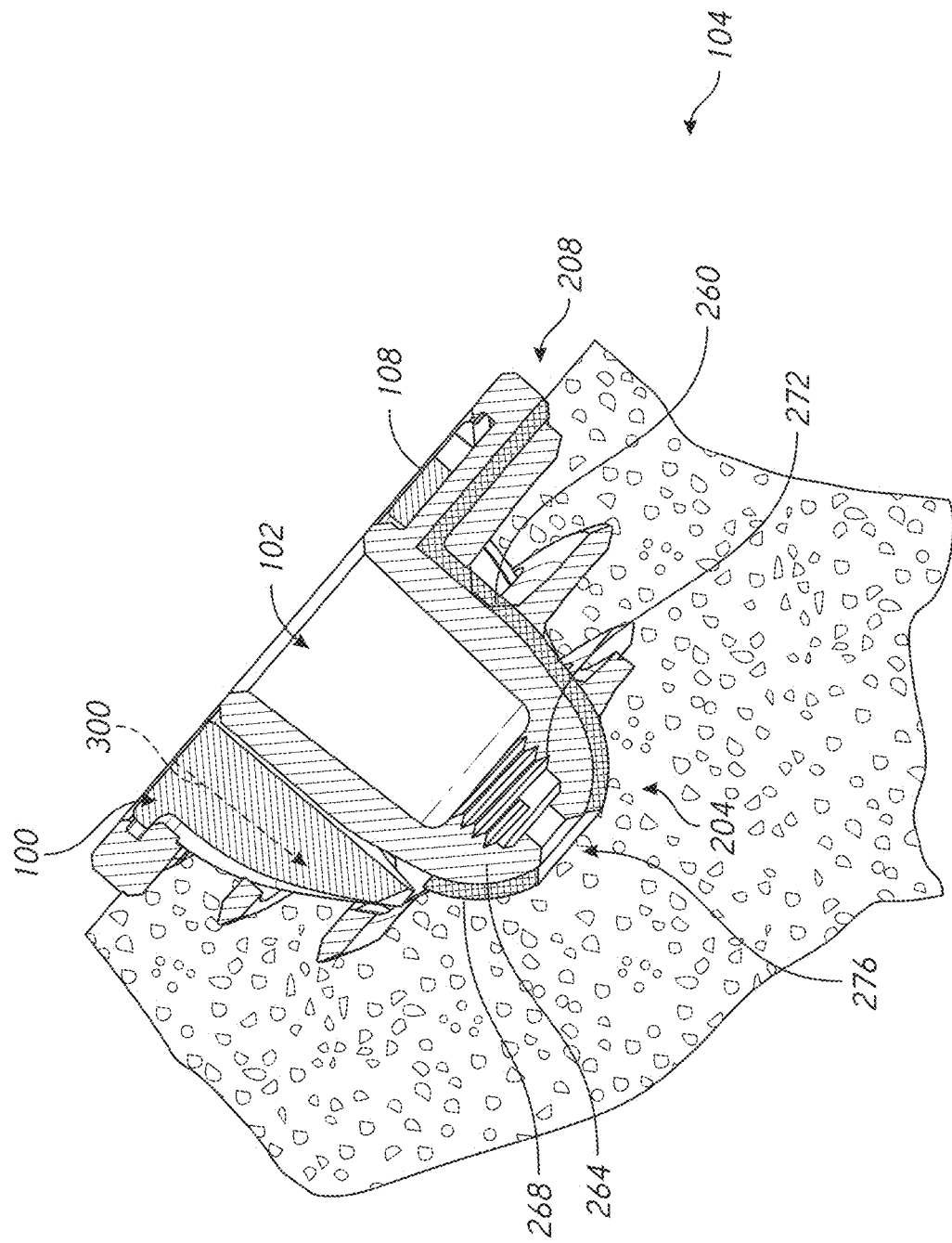
FIG. 7 is a cross-sectional view of the stemless shoulder assembly of FIG. 2 with the assembly disposed in the humeral head.

FIGS. 1B and 7 show the shoulder assembly 100 applied to a shoulder joint. FIG. 2A shows an exploded view of a shoulder assembly 100A that is similar to the shoulder assembly 100 except as described differently below. The description of the features of the shoulder assembly 100 that are present in or consistent with the shoulder assembly 100A shall be incorporated into the description of shoulder assembly 100A even if not explicitly repeated in connection therewith. The assembly 100 can provide secure stemless connection to the humerus H. The shoulder assembly 100 provides for simple implantation because a base member thereof can be directly threaded into cancellous bone without being mated to another pre-placed base member. The shoulder assembly 100 can be fully retained within a head h of the humerus H. FIG. 7 shows that the distal-most portion of the assembly 100 preferably can be disposed in the humeral head h. The assembly 100 does not have a stem or other member that protrudes beyond the head h into a medullary canal of the humerus. This approach is less invasive and simpler than procedures involving placement of a stem in a medullary canal. In other embodiments illustrated in part in FIG. 10 by the creation of a recessed surface s having a depth accommodating a thickness of a proximal portion of the assembly 100, the assembly 100 may be recessed within the humeral head of the humerus H such that a proximal face 105 the assembly 100 is flush with respect to a cut surface of the bone.

Figure 2:
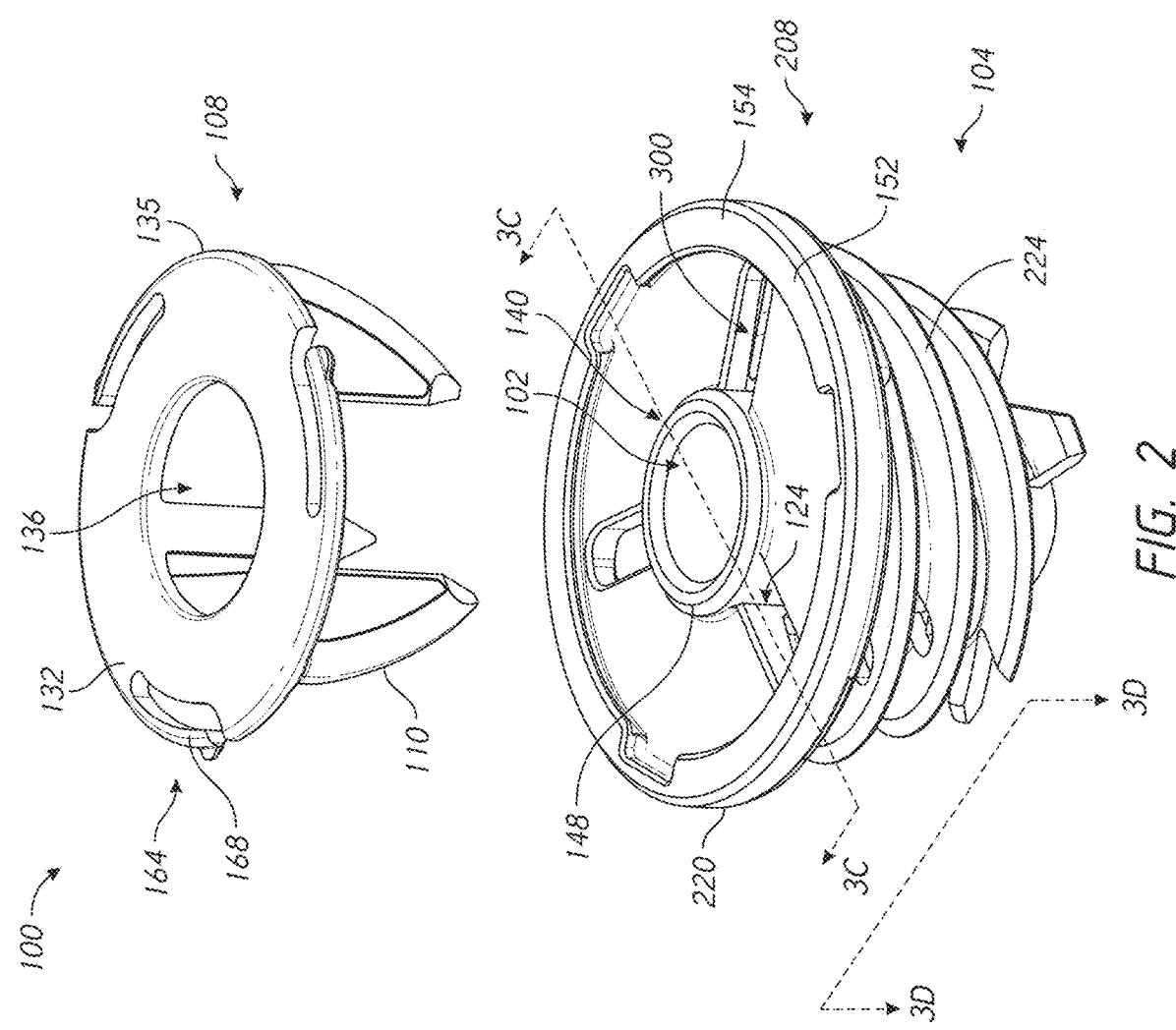
FIG. 2 is an exploded view of the stemless shoulder assembly shown in FIG. 1.
Figure 2A:
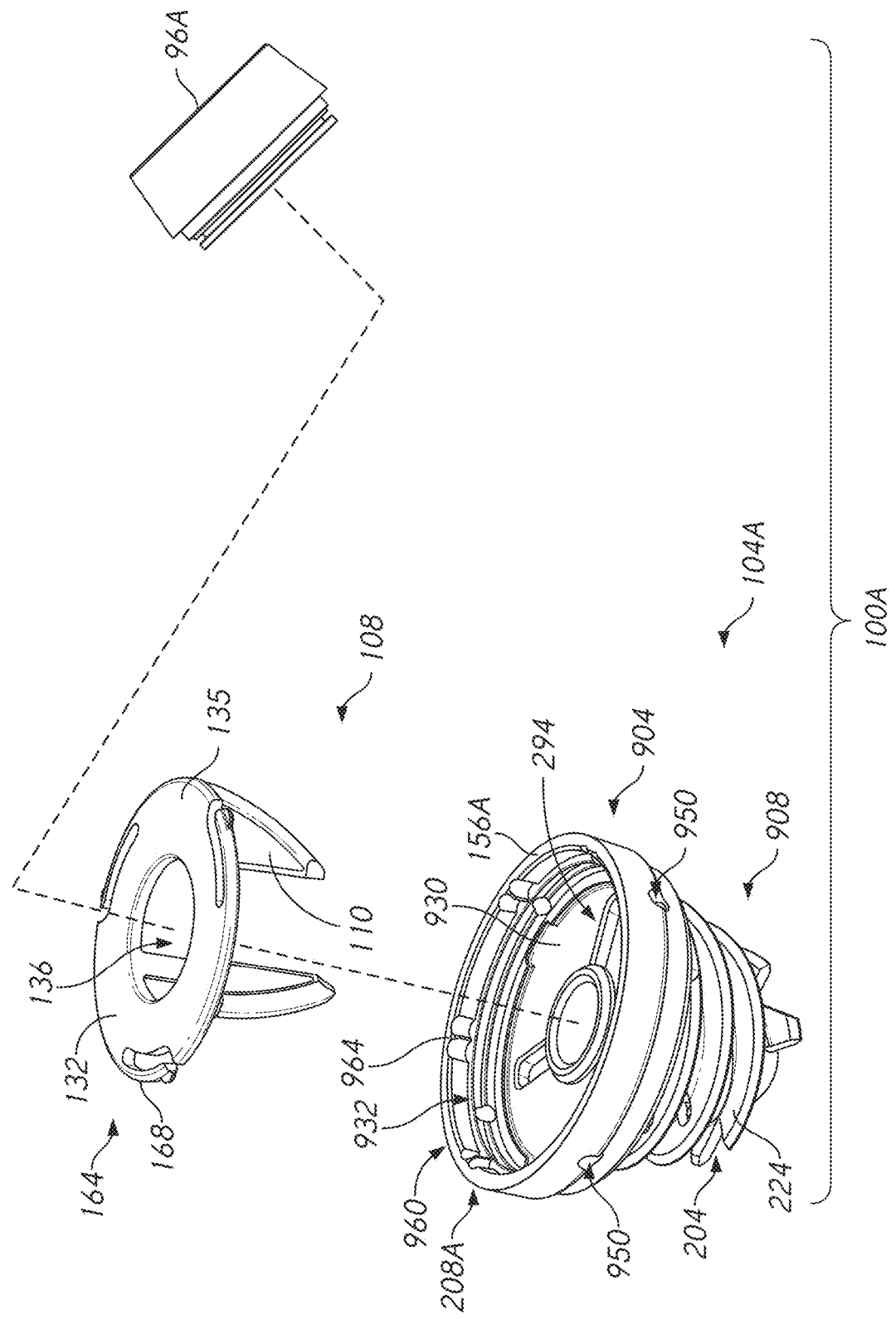
FIG. 2A is an exploded view of one of many combinations of stemless shoulder assemblies wherein the shoulder assembly includes a base member configured to be advanced into cancellous bone of the humerus and to be engaged directly with a reverse articular component.

FIG. 2 shows that the assembly 100 includes a base member 104 and a locking device 108. The base member 104 is advanced into a bony structure such as cancellous bone in use. As discussed further below a bone surface may be exposed by resection or reaming, followed by threading of the base member 104 into a newly exposed bone surface. The assembly 100 also includes the locking device 108. The locking device 108 includes a plurality of arms 110. In particular, the arms 110 extend outward or distal from proximal support 132. The arms 110 can include a first arm, a second arm, and a third arm. The arms 110 can be circumferentially spaced equal distances from each other, e.g., about 120 degrees apart in one embodiment. In another variation, the arms 110 include three arms, with two of the three arms spaced 90 degrees from each other and a third arm spaced 135 degrees from one of the other two arms. The locking device 108 may include four or more arms 110. If the arms 110 include four arms, the arms can be circumferentially spaced 90 degrees apart. If the arms 110 include two arms, the arms can be circumferentially spaced 180 degrees apart. The arms 110 are advanced through apertures 124 in the base member 104. In one embodiment, it should be noted that the number of arms 110 corresponds to an equal number of apertures 124. When so advanced, the arms 110 are disposed within the base member 104 in a manner that the arms 110 cross a space between portions, e.g., successive portions, of the base member 100. When so positioned, the arms 110 are also disposed within bone. Thus, two zones of the arms 110 can cross successive or adjacent portions of the base 104 and an intervening portion of the arms 110 can cross bone in a space between the successive or adjacent portion of the base. In this position, the arms 110 control, e.g., resist, rotation of the base member 104 relative to the bone such that the shoulder assembly 100 is secured against backing out of the bone upon implantation.

FIG. 2 also shows that the locking device 108 also includes a proximal support 132. The proximal support 132 is coupled with the arms 110 in a manner discussed further below. The proximal support 132 has a central aperture 136 disposed within an inner periphery thereof and extends outward from the central aperture 136 to an outer periphery 135. The inner and outer periphery of the proximal support 132 are received in a recess 140 formed in the base member 104. In one configuration the recess 140 and the proximal support 132 are configured such that a flush connection is provided between the proximal support 132 and the proximal face of the base member 104. The proximal support 132 can be connected to the base member 104 in an at least partially recessed position in the proximal face of the base member as discussed further below in connection with FIG. 6A.

Figure 3A:
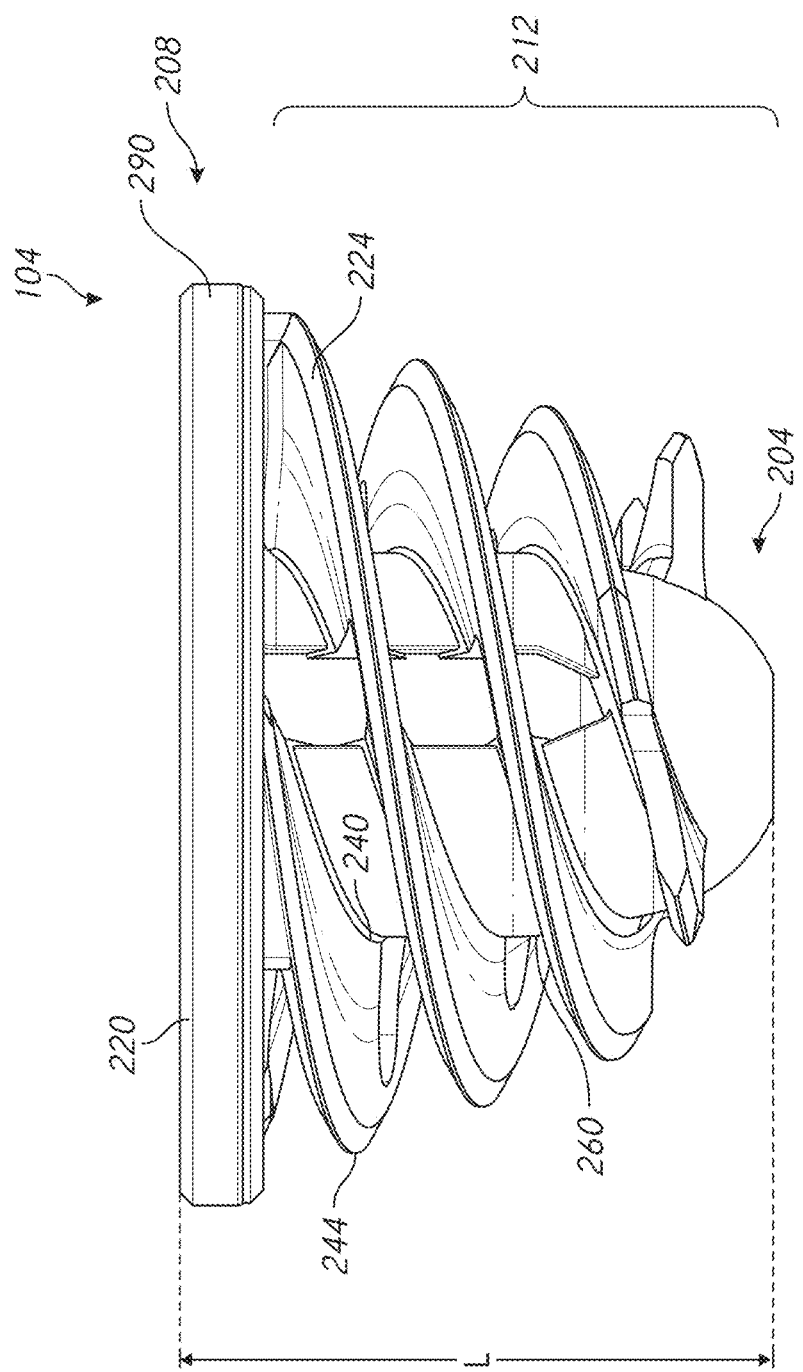
FIG. 3A is a side view of the base member of FIG. 2.
Figure 3B:
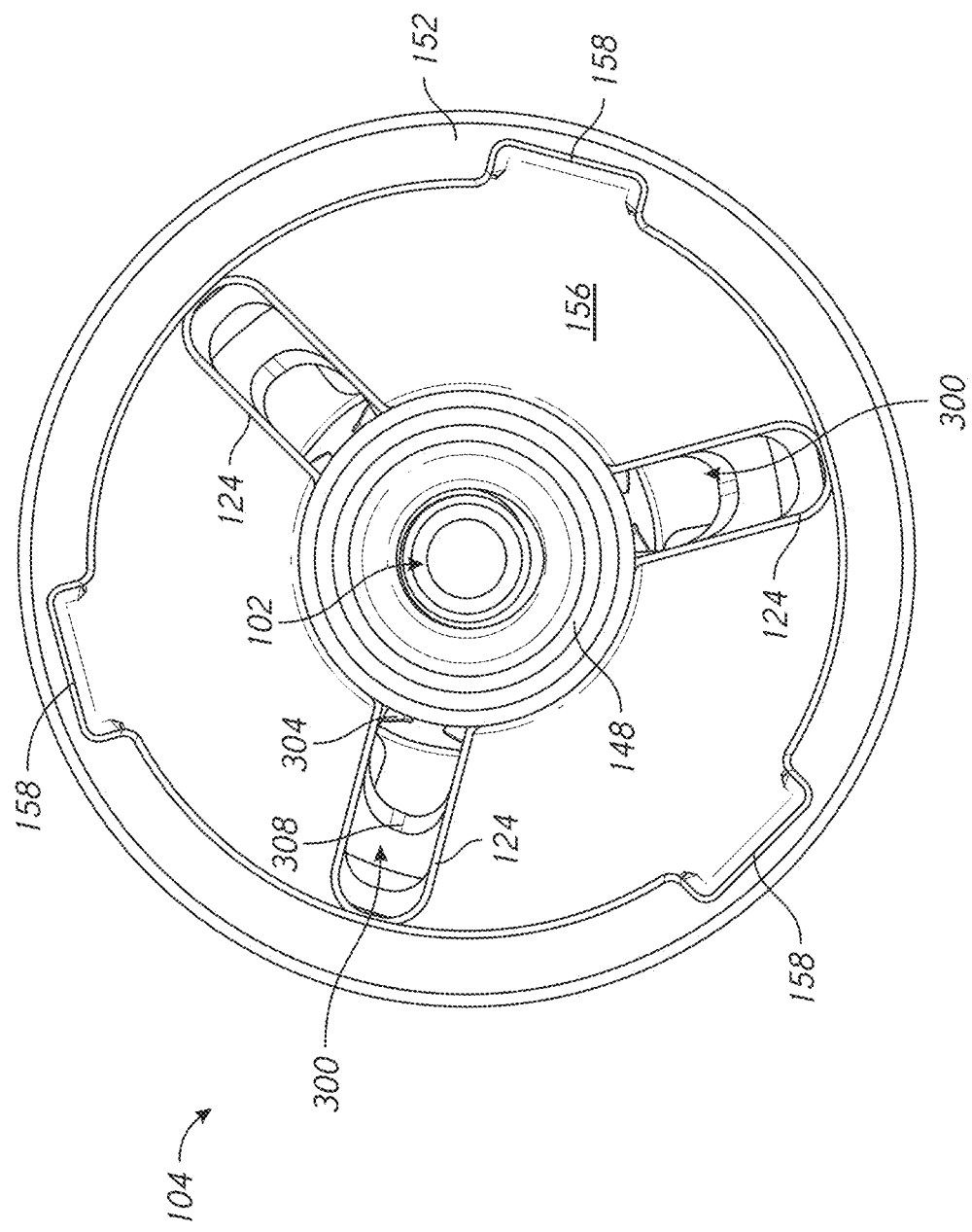
FIG. 3B is a top view of the base member of FIG. 2.

FIGS. 2 and 3B show that the proximal face of the base member 104 can include a raised inner portion 148 and a raised outer portion 152. The outer raised portion 152 extends around an outer periphery 154 of the base member 104. The raised portions 148, 152 are proximally oriented projections relative to a recessed surface 156. The recessed surface 156 can be disposed distally of one or both of the inner portion 148 and the outer portion 152. The raised inner portion 148 can define an aperture for access into the recess 102, which is configured for mating with articular components as discussed below. Each of the raised inner portion and the raised outer portion 148, 152 can comprises annular structures. The recessed surface 156 can comprise an annular portion. The apertures 124 can be formed in the recessed surface 156. In one embodiment the apertures 124 extend radially between the inner raised portion 148 and the outer raised portion 152. The apertures 124 can extend from the inner raised portion 148 to the outer raised portion 152. FIG. 2A shows that in one embodiment a raised outer portion 156A can be raised to a much greater extent than the raised inner portion 148. The raised outer portion 156A can be raised sufficiently to receive an inferior portion of an insert 96A as discussed further below. The raised outer portion 156A can overlap an inferior peripheral surface of the insert 96A to engage the insert as discussed below.

FIG. 3B shows that the proximal face of the base member 104 also can include a tool interface 158 that enables the base member to be advanced by an inserter into bone, as discussed below in FIG. 14. The tool interface 158 includes three notches in an inward side of the outer raised portion 152. In other embodiments, the tool interface 158 can include apertures in the recessed surface 156, notches in the inner raised portion 148, projections from any surface of the proximal face of the base member 104 or any combination of these features. Also, the tool interface 158 can provide access for a removal tool to engage the locking device 108. As discussed below, the locking device 108 includes a spring arm 168 and a removal tool can be applied at the tool interface 158 to compress the arm 168 to disengage the locking device from the base member 104. In some cases, an inserter tool can engage one or more apertures 124 in the base member 104 upon insertion.

One or more structures for securing the locking device 108 to the base member 104 or to the low profile base member 104A can be provided as discussed further below. For example the locking device can have an engagement feature 164 disposed on the proximal support 132 that is adapted to engage a corresponding feature on the proximal face of the base member 104 or on the low profile base member 104A. The engagement feature 164 can include an actuatable member that can move into a secure position relative to the recess 140 of the base member 104 or the low profile base member 104A. As discussed below in connection with FIGS. 5 and 6A, the engagement features 164 can include a spring arm 168 to engage an overhang of the recess 140. As shown in FIG. 2, one embodiment comprises a plurality of actuatable members, e.g., a plurality of spring arms 168. The spring arms 168 can be spaced apart, e.g., providing equal angle separation between adjacent spring arms 168. In one embodiment, the number of spring arms 168 matches the number of arms 110. Each spring arm 168 can be spaced apart from each arm 110 as discussed further below.

In another embodiment, a serration 172 is provided between the arms 110 of the locking device 108 and the base member 104 or the low profile base member 104A as discussed in greater detail below in connection with FIG. 6B. The serration 172 is an example of a one-way connection that can be provided between the arms 110 and the base member 104. Other one-way connections can be provided in addition or in place of the serration 172, such as a ratchet, a barb, or one or more spring arms.

FIGS. 2-3B show further details of embodiments of the base member 104 and the low profile base member 104A. In some embodiments, the base member 104 can include various features described in PCT publication WO2016/094739, the entirety of which is hereby incorporated by reference herein. The base member 104 has a first end 204, a second end 208 and a body 212 that extends between the first end 204 and the second end 208. The base member 104 can comprise a length L between the first end 204 and the second end 208 that is less than a dimension of an articular surface of typical epiphysis to a medullary canal of a typical humerus. The base member 104A can comprise a length L between the first end 204 and the second end 208A that is less than a dimension of a corresponding dimension from the first end 204 of the base 104 of the assembly 100 to the superior edge of the tray 94. FIGS. 18A and 18B show that the length L of the low profile base member 104A can be greater than that of the base member 104. But, the shoulder assembly 100A is able to provide an overall lower profile to an associated articular surface as discussed further below. The first end 204 can be disposed within the epiphysis when the second end 208 is at a surface of the bone, as shown in FIG. 7. The second end 208 can be disposed at or on a superior medial resection plane of a humerus while the first end 204 is well within the epiphysis. This enables the first end 204 to stop short of a medullary canal of the humerus when the base 104 is fully implanted, which allows the bone between the first end 204 and the medullary canal to remain unaltered and also simplifies the procedure to the extent that any normal access to and preparation of the medullary canal is not needed. The second end 208A is generally higher above the resection plane of the humerus than is the second end 208 as shown by comparison of FIGS. 7 and 7A by virtue of a cylindrical member 908 disposed at the superior end of the base 104A. The additional height of the cylindrical member 908 of the base 104A enable the base 104A to directly receive and engage an inferior portion on an insert 96 as discussed further below. In various embodiments, the length L can be between about 15 mm and about 30 mm, between about 18 mm and about 25 mm, between about 18 mm and about 24 mm, between about 21 mm and about 27 mm, between about 24 mm and about 29 mm, or between about 30 mm and 40 mm. The length L can be about 18 mm, about 21 mm about 23 mm, about 24, mm about 26 mm about 29 mm, and about 34 mm. In one approach, at least a portion of the assembly 100 or the shoulder assembly 100A is patient specific. For example, the length L can be defined for a specific patient based on pre-operative planning, such as using two dimensional or three dimensional imaging. The base member 104 or the low profile base member 104A can thereafter be manufactured for that patient based on the determined dimension L.

The base member 104 can include a collar 220 and a helical structure 224. The helical structure 224 is disposed about a cylindrical portion 260 of the body 212 of the base member 104. In some embodiments, the helical structure 224 extends directly from the body 212 and may be considered threads of the body 212. The helical structure 224 can include one or a plurality of threads, e.g., two, three, four, or more threads, disposed between the first end 204 and the second end 208. The threads can start adjacent to the first end 204 and extend toward, e.g., entirely to the second end 208. FIG. 3A shows that the threads or other helical structure 224 can end at or adjacent to the collar 220. The threads or other helical structure 224 can have inner portions 240 disposed at or on the body 212 about the recess 102 and outer portions 244 disposed along the periphery of the base 104. FIG. 3A shows that the helical structure 224 has a width defined as the distance between the inner and outer portions 240, 244 that is large, e.g., comprising more than one-quarter of, e.g., about one-third of, the width of the base 104 at a given location. These large threads or other helical structure 224 ensure large purchase in the bone. Large purchase provides strong resistance to pullout even prior to any bone ingrowth into the surfaces of the shoulder assembly 100. Generally one or more surfaces of the shoulder assembly 100 that are in direct contact with bone may be textured e.g., coated or layered with a porous material in order to accelerate tissue ingrowth such as bony ingrowth. Therefor good initial resistance to pull-out is advantageous for the patient. At least one turn of a thread or other helical structure 224 completely surrounds the recess 102, e.g., by completely surrounding the body 212, in some embodiments.

The body 212 surrounds the recess 102, which is configured to mate with an articular component, such as humeral head or a glenoid sphere. In one embodiment, the body 212 includes a cylindrical portion 260 within which the recess 102 is disposed. The cylindrical portion 260 can have any suitable outside configuration, such as including a textured surface that is well suited to encourage bony ingrowth. The cylindrical portion 260 can include a generally tapered profile in which a portion at or adjacent to the first end 204 of the base member 100 has a first width and a portion at or adjacent to the second end 208 of the base member 100 can have a second width, the second width being greater than the first width. In some embodiments, the cylindrical portion 260 is generally rounded and formed a blunt but tapered profile. The cylindrical portion 260 can have a flat distal surface in some embodiments.

FIG. 7 shows that the cylindrical portion 260 can include a plurality of layers. For example, an inner layer 264 can be disposed adjacent to the recess 102. The inner layer 264 can include the surface surrounding the recess 102 and can extend away from that surface toward an outer surface of the cylindrical portion 260. In one embodiment an outer layer 268 can be disposed adjacent to the outer surface of cylindrical portion 260. The outer layer 268 can extend from the external surface of the cylindrical portion 260 toward the recess 102. In one embodiment, the outer layer 268 is formed directly on the inner layer 264 although other arrangements are possible as well. The outer layer 268 can be a porous structure that is suitable for bony ingrowth.

FIG. 7 also shows that a tool interface 272 can be disposed at or adjacent to the first end 204 of the base member 104. The tool interface 272 can include a threaded portion that can mate with a delivery tool, as discussed further below. A lumen 276 can be provided at the first end 204 such that access can be provided from the first end 204 through the wall of the cylindrical portion 212 into the recess 102. The lumen 276 and recess 102 together provide access for a K-wire or other guiding device such that implanting the base member 104 can be controlled in an appropriate manner.

Figure 6A:
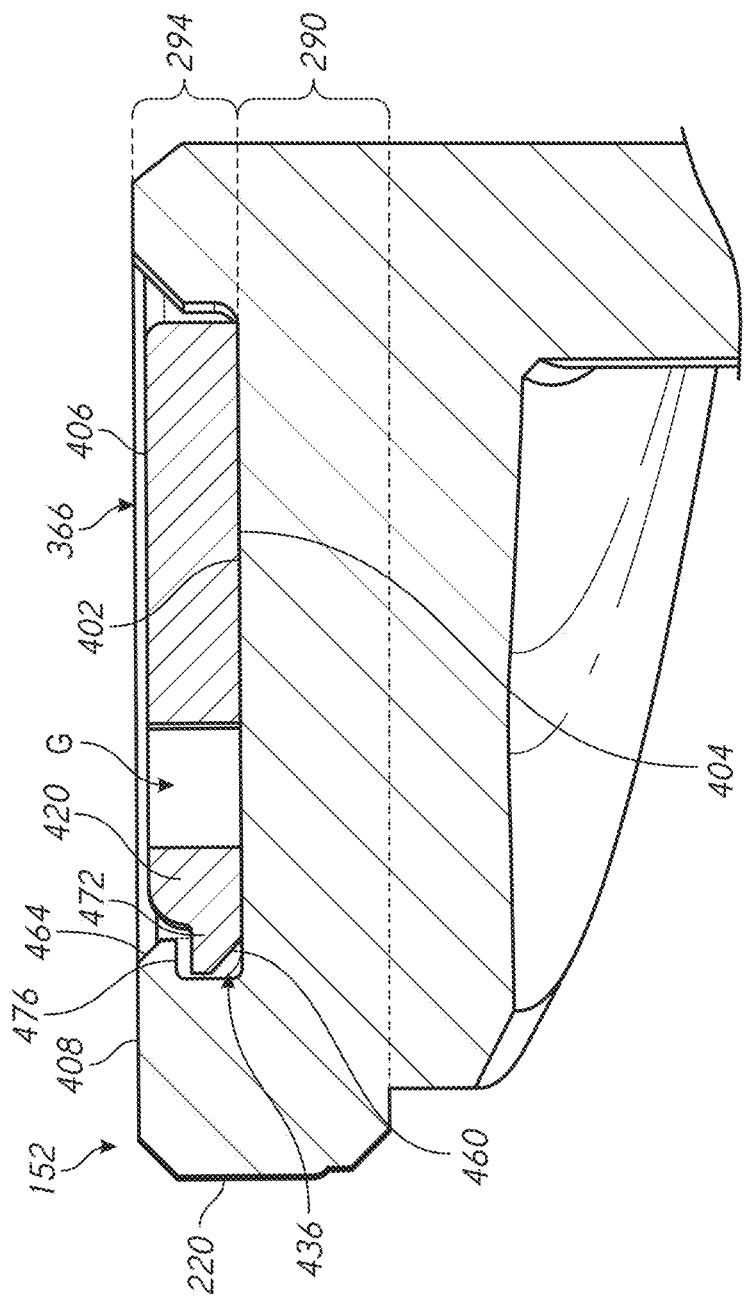
FIG. 6A is a detail view of one embodiment of an engagement feature that causes the locking component of FIG. 4 and the base member of FIGS. 3A and 3B to be engaged.
Figure 7A:
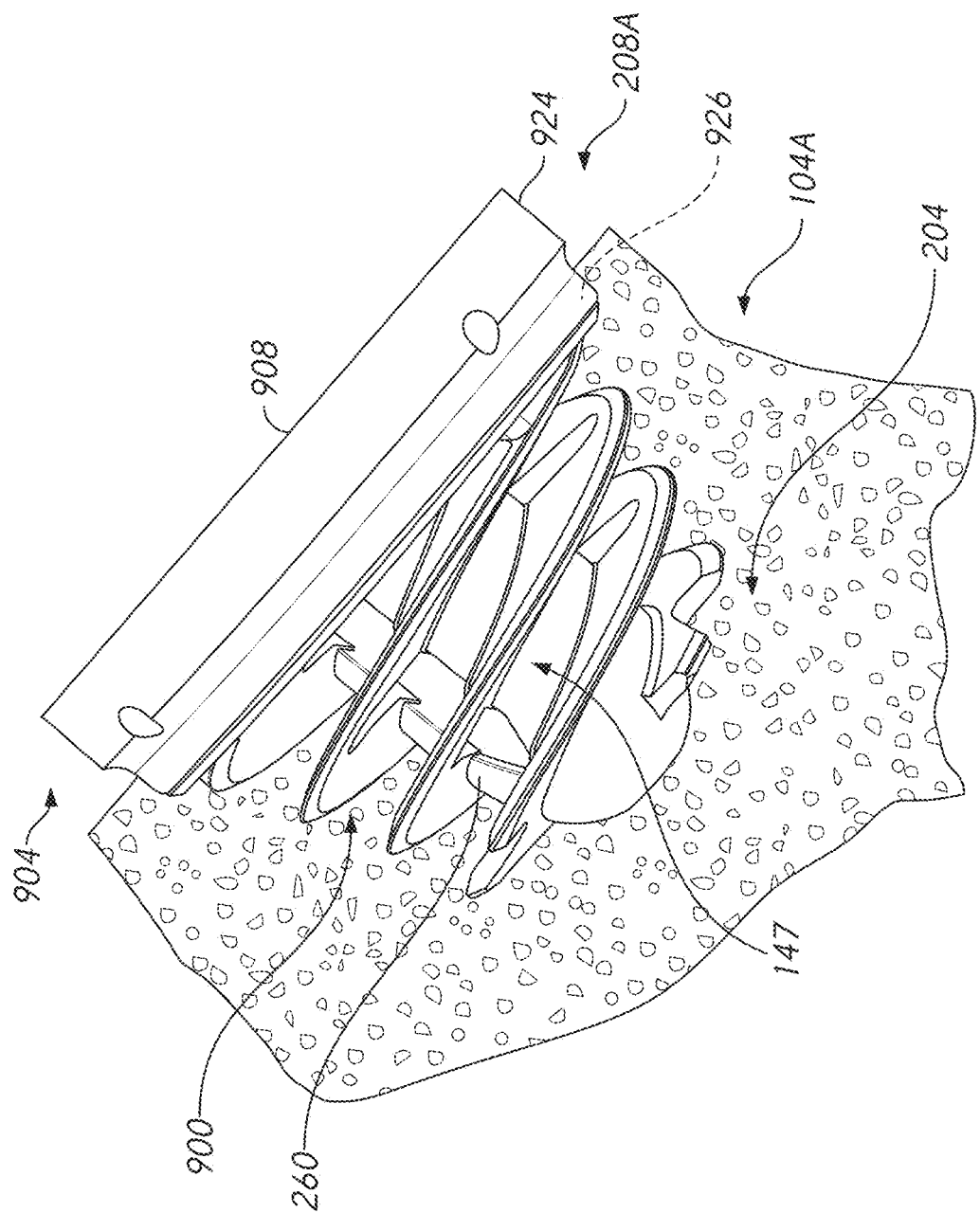
FIG. 7A is a schematic view showing the base member of the kit of FIG. 2A disposed in a resected humeral head.

The collar 220 can be disposed at or can comprise the second end 208 of the base member 104. The collar 220 can have a transverse width, e.g., a diameter that is suitable for a given condition. For example, the diameter of the collar 220 can be selected such that the entire outer periphery of the base 104 is within the bone exposed by resection and/or recessed into such an exposed bone portion, e.g., as illustrated in FIGS. 8-12. The diameter of the cylindrical member 908 can be selected such that the entire outer periphery of the low profile base member 104A is within the bone exposed by resection and/or recessed into such an exposed bone portion, e.g., as illustrated in FIGS. 7A and 14A and corresponding descriptions herein. In some embodiments the collar 220 or the cylindrical member 908 has a diameter of more than about 25 mm and less than about 60 mm. The collar 220 or the cylindrical member 908 can have a diameter of between about 30 mm and about 45 mm. The collar 220 or the cylindrical member 908 can have a diameter of about 33 mm in one embodiment. The collar 220 or the cylindrical member 908 can have a diameter of about 42 mm in one embodiment. Making the collar 220 or the cylindrical member 908 as large as possible within such bounds provides for better load transfer between the collar 220 or the cylindrical member 908 and the humerus H. In one approach, the diameter of the collar 220 or the cylindrical member 908 can be defined for a specific patient based on pre-operative planning, such as using two dimensional or three dimensional imaging. The base member 104 or the low profile base member 104A can thereafter be manufactured for that patient based on the determined diameter of the collar. For example, the diameter of the collar 220 or the cylindrical member 908 can be selected such that the collar covers the cortical rim exposed by resection. The collar 220 or the cylindrical member 908 can attach to or can be integrally formed with the cylindrical portion 260 of the body 212. In one embodiment the collar 220 or the cylindrical member 908 comprises a transverse flange 290 that extends outward of the recess 102 that is also disposed at the second end 208. An inner portion of the flange 290 can be disposed adjacent to the recess 102 and can include the inner raised portion 148. An outer portion of the flange 290 can be disposed outward of the inner portion. The flange 290 can define the proximal face of the base member 104 or of the low profile base member 104A. The flange 290 can accommodate the proximal support 132 of the locking device 108. FIG. 6A shows that in some embodiments, the flange 290 can at least partially surround a space 294 disposed therein to receive a portion of the locking device 108. The space 294 can be an annular recess located proximal of the recessed surface 156 and between the inner portion 148 and the outer portion. The space 294 can be bounded by an inner edge of the outer portion 152 and an outer edge of the inner portion 148. Comparing FIGS. 2 and 2A, the space 294 can be seen to be much deeper in the low profile base member 104A such that the space 294 can accommodate an inferior portion of the insert 96 as discussed further below. The flange 290 can engage the spring arm 168 of the locking device 108 in the space 294 such that the locking device 108 will not be inadvertently disengaged from the base 104 or from the low profile base member 104A and protrude from or be removed from the space 294.

Figure 3C:
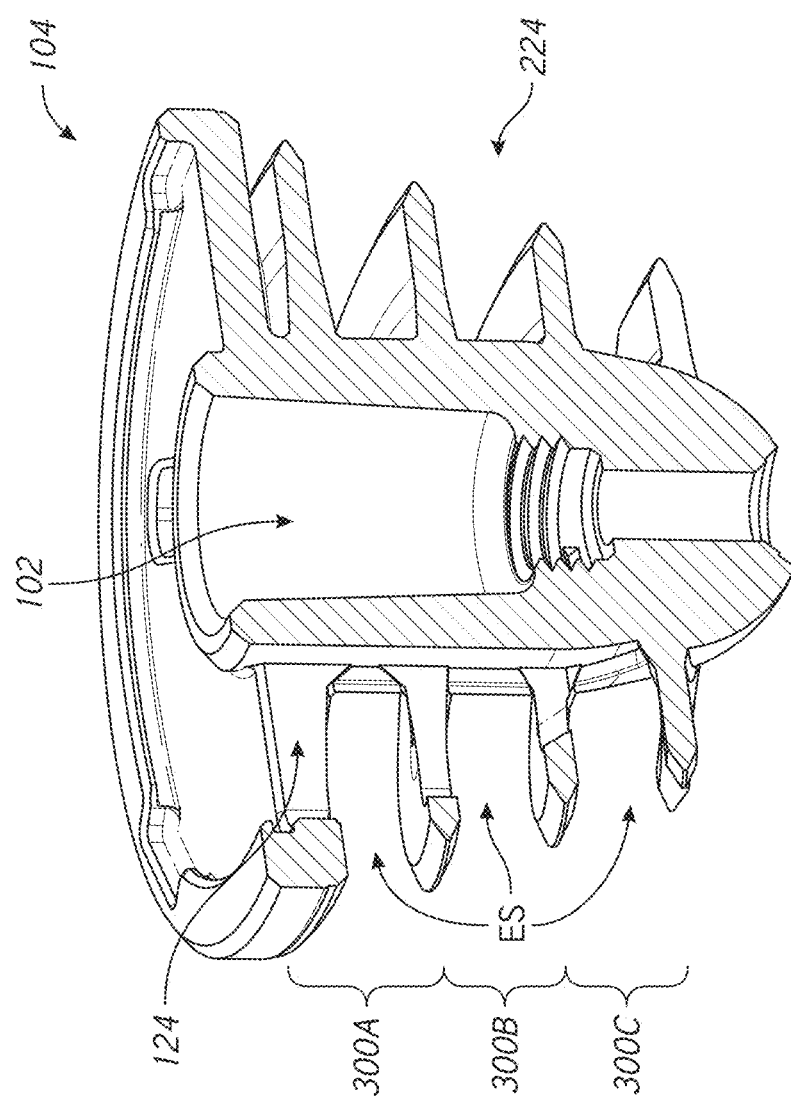
FIG. 3C is a cross-sectional view of the base member of FIG. 2 taken at section plane 3C-3C.

FIGS. 2, 2A, and 7 show that in some embodiment, the shoulder assembly 100 and the shoulder assembly 100A includes a pathway 300 that projects distally of the collar 220. The pathway 300 can comprise a first pathway. The shoulder assembly 100 or the shoulder assembly 100A can include a plurality of pathways, 300 with each pathway corresponding to an arm 110 of the locking device 108. FIG. 3B shows that the base 104 can define a plurality of such pathways, e.g., two or three pathways configured to receive corresponding arms 110. There can be four or more than four pathways 300. The pathway 300 can have a first end located at the opening or apertures 124 in the collar 220 or of the cylindrical member 908. The pathway 300 can continue down through the base member 104 or the low profile base member 104A. FIG. 3C shows that the pathway 300 can have one or more segments disposed through the helical structure 224. A first segment 300A of the pathway 300 extends from the aperture 124 to a first portion, e.g., a proximal-most turn or portion of the helical structure 224 immediately distal of the collar 220, e.g., immediately distal of one of the apertures 124. A second segment 300B of the pathway 300 extends from the first segment 300A to a second turn or portion of helical structure 224 immediately distal of the first portion of the helical structure. A third segment 300C of the pathway 300 can extend from the second segment to a third turn or portion of helical structure 224 immediately distal of the second portion of the helical structure 224. The low profile base member 104A can have one or a plurality of, e.g., three, pathways 300 which can have segments as described above.

Figure 3D:
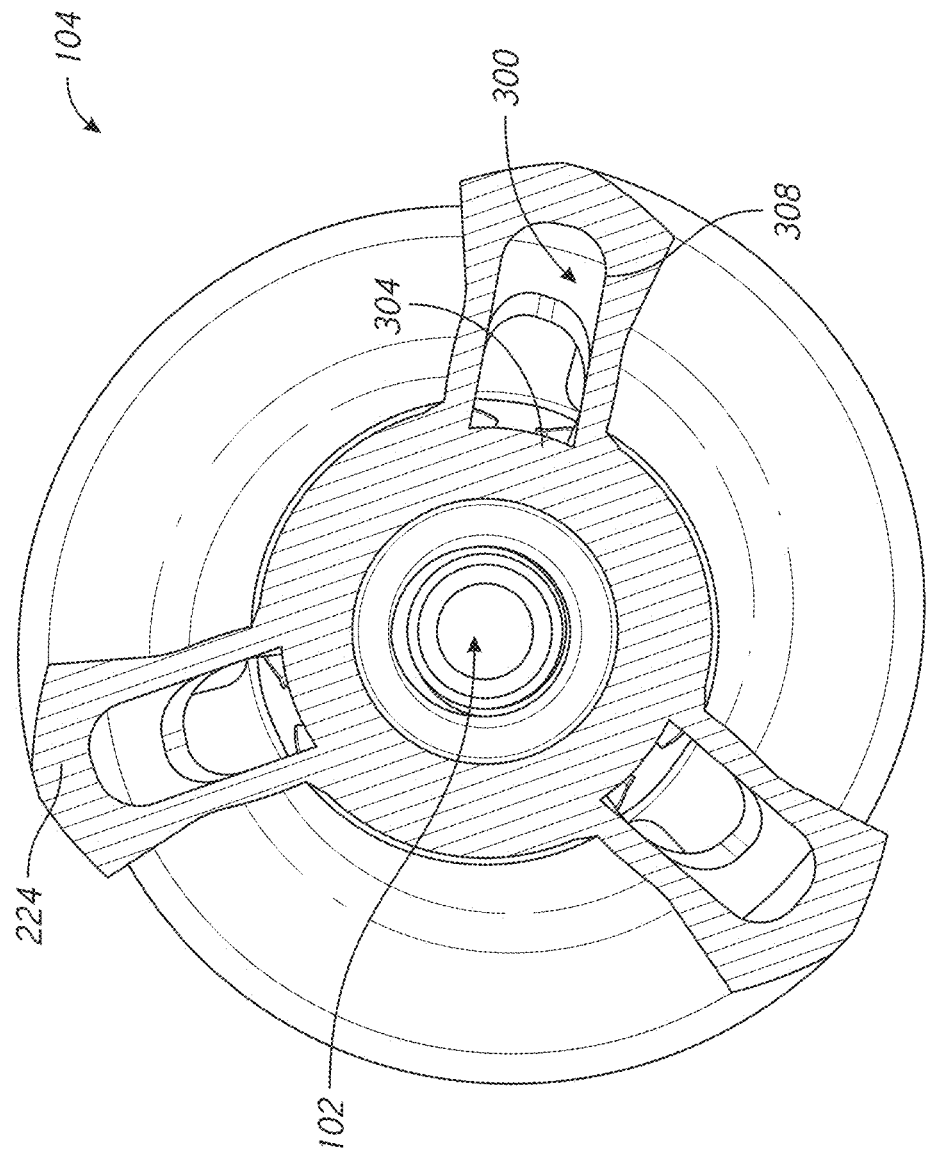
FIG. 3D is a cross-sectional view of the base member of FIG. 2 taken at section plane 3D-3D.

FIGS. 3A and 3D illustrate that at specific locations along the length of the base 104 from the first end 204 to the second end 208, the pathway 300 can have a first boundary 304 corresponding to an outer surface or layer of the cylindrical portion 260, for example corresponding to a surface of the outer layer 268. The pathway 300 can have a second boundary 308 at a same location along the length of the base 104 from the first end 204 to the second end 208 formed by an adjacent portion of helical structure 224. The second boundary 308 can include a U-shaped opening in the inner portion 240 of the helical structure 224. The U-shaped opening in the inner portion 240 can extend across the width of the helical structure toward the outer portion 244 of the helical structure 224. The U-shaped opening can extend 25%, 35%, 45%, 50%, 60%, 70%, 75% or up to 90% of the distance across the width of the helical structure 224 from the inner portion 240 toward the outer portion 244. In one embodiment, the helical structure 224 has a tapered configuration in which transverse distance between opposite sides of the helical structure 224 is decreased in the direction of the first end 204 compared to the same dimension toward the second end 208. The length of the U-shaped opening in successive portions of the helical structure 224 in the direction toward the first end 204 is progressively less in some embodiments. As a result the width bounded by a turn of the helical structure 224 and the cylindrical portion 260 in the first segment 300A of the pathway 300 can be greater than the width bounded by a turn of the helical structure 224 and the cylindrical portion 260 in the second segment 300B. The width in the second segment 300B can be greater than the width in the third segment 300C bounded by a turn of the helical structure 224 and the cylindrical portion 260. This configuration is advantageous in accommodating embodiments of the locking device 108 having arms 110 that are tapered as discussed further below.

The pathway 300 can extend through one or more spaces between adjacent threads of the helical structure 224. The pathway 300 can comprise two or more segments surrounded by portions of the base member 104 and at least one exposed segment ES. The exposed segments comprise portions of the first and second segments 300A, 300B and between the second and third segments 300B, 300C in some embodiment. The exposed segments ES are exposed in that, unlike the segments 300A, 300B, 300C, the exposed segments of the pathway 300 are not enclosed circumferentially and thus bone disposed within the helical portion 224 can directly contact the arms 110 in the exposed segment. As such the pathway 300 is bounded by bone matter in the exposed segments.

Figure 4:
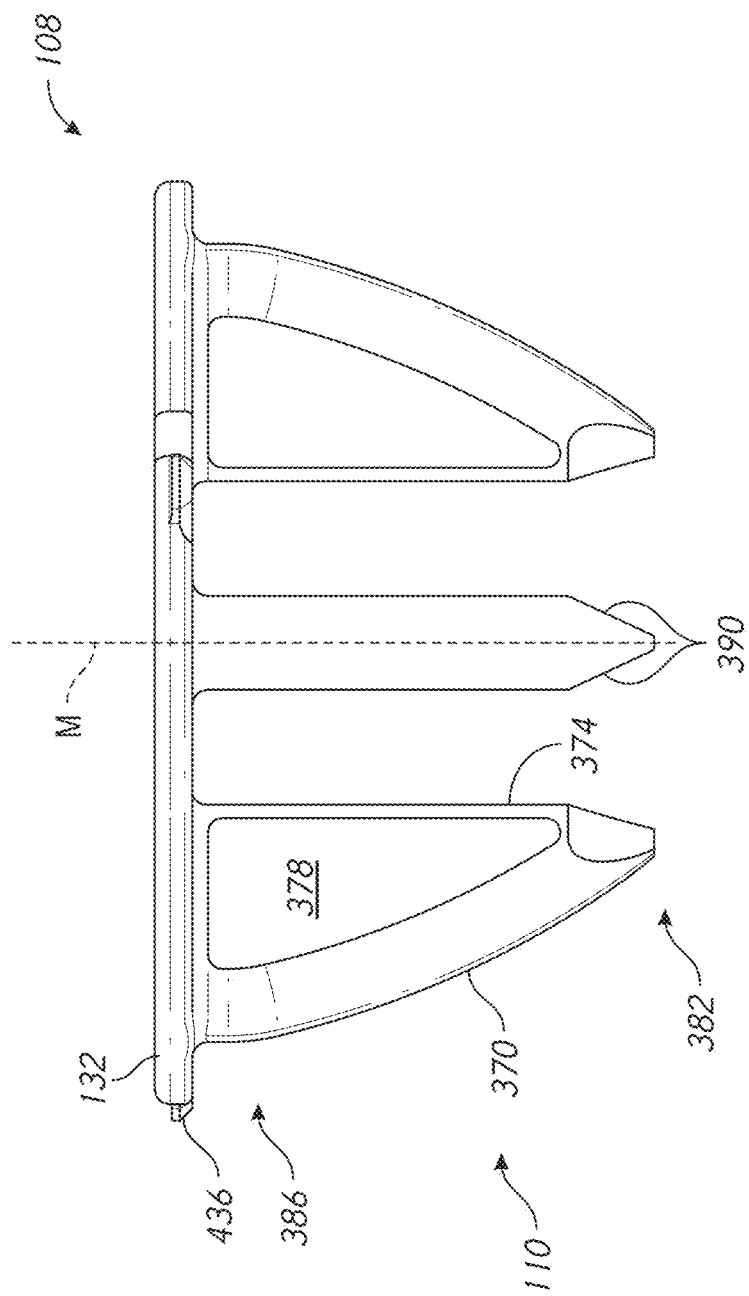
FIG. 4 is a side view of one embodiment of a locking component, which is a component configured to control, e.g., reduce or eliminate and/or control rotation of a base member or of a helical structure of a prosthesis assembly.
Figure 5:
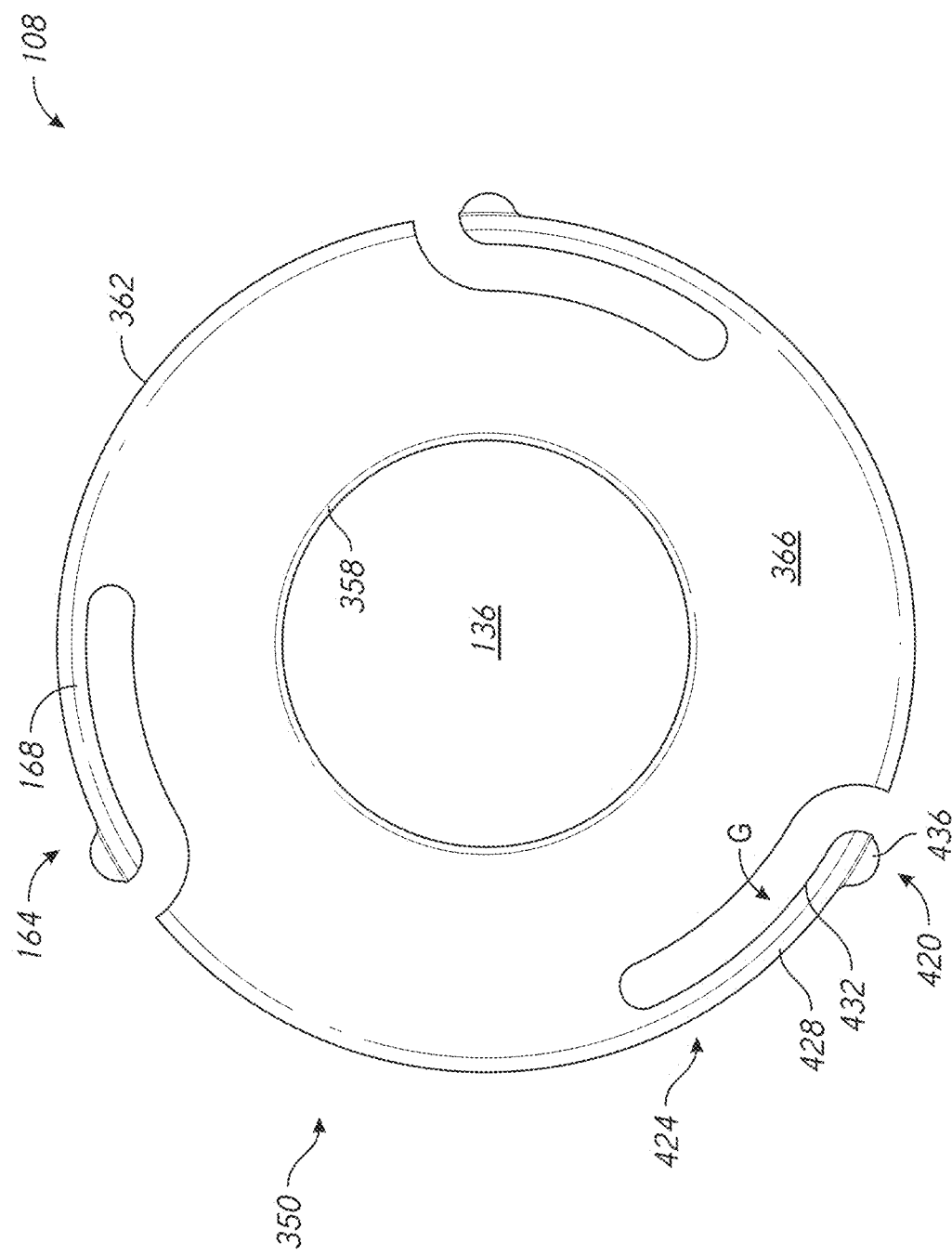
FIG. 5 is a top, proximal side, or medial side view of the locking component of the FIG. 4.

FIGS. 2, 4 and 5 show the locking device 108 in detail. As discussed above, the locking device 108 has a proximal support 132 and a first arm 110 that projects distally of the proximal support 132. The proximal support 132 includes an inner periphery 358, an outer periphery 362 and an annular member 366 disposed therebetween. The inner periphery 358 surrounds the central opening 136, which is sized to receive the inner raised portion 148 of the base member 104 if present. The annular member 366 is configured to be received in the recess 140, as discussed above.

The first arm 110 is configured to be disposed in the first pathway 300. The pathway 300 projects distally of the collar 220. The first arm 110 is disposed distal of the collar 220 when the proximal support 132 is disposed adjacent to a proximal side of the collar 220 and the first arm 110 is in the first pathway 300.

The first arm 110 includes an outer edge 370, an inner edge 374 and a span 378 disposed therebetween. The first arm 110 includes a first end 382 disposed away from the support 132 and a second end 386 disposed adjacent to and in some cases directly coupled to the support 132. The first arm 110 can be tapered, for example with the outer edge 370 approaching the inner edge 374 in the direction toward the first end 382 and/or with the outer edge 370 diverging away from the inner edge 374 in the direction toward the second end 386. In one embodiment, opposite faces 390 of the span 378 are also tapered with at least one of, e.g., both of, the opposite faces 390 approaching a longitudinal mid-plane M of an arm 110. The tapering of the arms between the edges 370, 374 facilitates providing a tapered profile in the base member 104. The tapering of the arms between the edges 370, 374, sometimes referred to herein as a radial taper, facilitates insertion of the first end 382 into the aperture 124 because the first end 382 is much narrower in the dimension between the edges 370, 374 than the aperture 124 is in the radial direction. The tapering of the arms 110 between the faces 390, sometimes referred to herein as a circumferential taper, facilitates insertion of the first end 382 into the aperture 124 because the first end 382 is much narrower in the dimension between the faces 390 than the aperture 124 is in the circumferential direction.

At least one of the circumferential and radial tapers of the arms 110 enables the locking device 108 to easily be advanced through bone matter that is disposed along the pathway 300.

As discussed above, the first arm 110 is disposed through bone in the space between successive portions of the helical structure 224, e.g., in the first segment of the path 300 and in the second segment of the path 300, when the humeral shoulder assembly is implanted. The span 378 and/or other parts of the arms 110 can be porous to enhance bony ingrown when the assembly 100 is implanted. The porous properties can be provided by a porous metal surface or structure or by other porous layers disposed on an underlying layer of metal or another material. At least the widening of the arms 110 toward the second end 386 increases the purchase of bone in the widened area, e.g., in the first segment of the path 300 and also in the second segment of the path 300 compared to an arm that is not tapered.

In some embodiments, the arms 110 are not tapered in the radial direction. For example the arms 110 can have a constant radial dimension between the edges 370 and 374 at a length between, e.g., along the entire length between, the first end 382 and the second end 386. In some embodiments, the arms 110 are not tapered in the circumferential direction. For example the arms 110 can have a constant circumferential dimension between the first end 382 and the second end 386.

As discussed above, the locking device 108 facilitates retaining the base member 104 in the bone at least by opposing, and in some cases completely preventing, rotation of the base member that would cause the base member to back out of the bone into which it has been advanced. Additionally, in some embodiments, it is beneficial to oppose, and in some cases completely prevent, axial movement of the locking device 108 away from the base member 104. At the extreme, such movement could result in the arms 110 of the locking device 108 completely coming out of the pathways 300 and, indeed, out of the base member 104 completely. It also may be desirable to prevent even lesser movements of the locking device 108 relative to the base member 104. As shown in FIG. 6A, a distal face 402 of the annular member 366 may be positioned in direct contact with a proximal face 404 of the transverse flange 290. Such contact can correspond to a proximal face 406 of the annular member 366 being distal of a proximal face 408 of the raised outer portion 152. By recessing the annular member 366, the interaction of the assembly 100 with the articular member of the kit 80 of FIG. 1 is controlled. For example, the annular member 366 will not impede advancement of the articular members into secure engagement with the recess 102.

FIGS. 5 and 6A illustrate various embodiments of axial locking configuration that can be provided in the shoulder assembly 100. An axial locking configuration can include the engagement feature 164 disposed on the proximal support 132. The spring arm 168 of the engagement feature can include a first end 420 disposed away from the annular member 366 and a second end 424 coupled with the annular member 366. The spring arm 168 also has an elongate portion 428 that extends between the first end 420 and the second end 424. The elongate portion 428 preferably has an arcuate form and can, in some embodiments, have the same curvature as a portion of the annular member 366 adjacent to the second end 424. The elongate portion 428 can be separated from the annular member 366 along a radially inner edge 432 of the elongate portion 428 by a gap G. The gap G and the length of the elongate portion 428 can be such that the first end 420 can be moved sufficiently to allow for a snap-fit connection as discussed further below. In one embodiment, the first end 420 of the spring arm 168 has a deflector 436 that facilitates movement of the elongate portion 428 and specifically movement of the first end 420. FIG. 6A shows that the deflector 436 can include an angled surface 460 that initially engages a corresponding angled surface 464 on the base member 104, e.g., on the raised outer portion 152 at the proximal face of the base member. As the arms 110 of the locking device 108 are advanced into the paths 300, the annular member 366 eventually is received in the space 294. At that time, the angled surfaces 460, 464 engage each other, which engagement causes the deflection of the first end 420 of the spring arm 168. The first end 420 is deflected radially inwardly such that the gap G is reduced at least at the first end 420. This allows a proximal facing surface 472 to move to a position distal of a distal facing surface 476. After the proximal facing surface 472 is at a position distal of the distal facing surface 476, the spring arm 168 resiliently moves the deflector 436 back to the configuration shown in FIG. 5. At this point, the proximal facing surface 472 is distal of and aligned with, e.g., positioned under, the distal facing surface 476, as shown in FIG. 6A. In this configuration, the proximal facing surface 472 blocks the distal facing surface 476 from moving proximally. Thus the surfaces 472, 476 prevent the locking device 108 from disengaging from the base member 104. Similar engagement between the locking device 108 and the low profile base member 104A can be provided within the cylindrical member 908.

Another advantageous aspect of the assembly 100 is that the locking device 108 can be quickly and easily disengaged from the base 104. The tooling interface 158 allows an extraction tool to be disposed between the raised outer portion 152 and the spring arm 168. The extraction tool can apply a radially inward force on an outer periphery of the elongate portion 428 of the spring arm 168. Compression of the spring arm 168 decreases the gap G as the proximal facing surface 472 is moved radially inward of the distal facing surface 476. Once the first end 420 is entirely radially inward of the distal facing surface 476, the engagement feature 164 is disengaged from the base 104. If more than one spring arm 168 is provided some or all of the spring arms can be compressed to allow the locking device 108 to be withdrawn from the base 104. The shoulder assembly 100A can be disassembled in a similar manner to remove the locking device 108 from the low profile base member 104A.

Figure 6B:
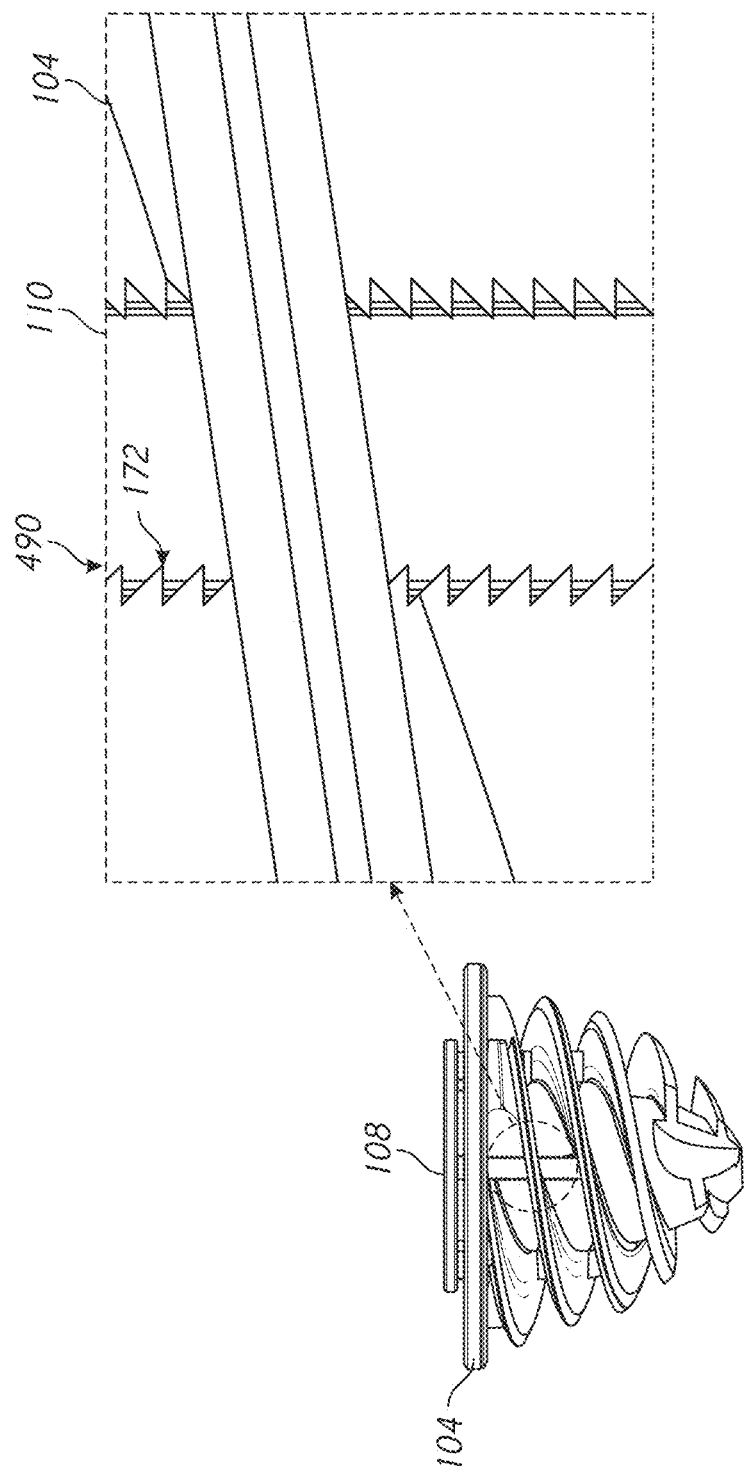
FIG. 6B is a detail view of another embodiment of an engagement feature that causes the locking component and the base member to be engaged at a location within the helical structure.

FIG. 6B shows additional axial locking configurations that can be provided in the shoulder assembly 100. In these embodiments, axial locking can occur at an interface 490 between one or more of the arms 110 and one or more of the pathways 300. For example, the serrations 172 discussed above can be provided at the interface. In one variation, serrations 172 are disposed along the pathway, e.g., on a surface of the cylindrical member 212 and/or on a surface of the helical structure 224. The serrations 172 can be placed at both the surface of the cylindrical member 212 and at the helical structure 224. In another embodiment, the serrations 172 could be provided on a surface of the arm 110, e.g., on one of the outer edge 370, the inner edge 374, and/or on one of the faces 390. The serrations 172 allow for relatively easy insertion of the arms 110 but bite into and oppose withdrawal of the locking device 108 to oppose axial disengagement of the locking device 108 from the base member 104. The locking device 108 can be secured to the low profile base member 104A using the serrations 172 in a similar manner.

The serrations 172 can be disposed along the entire length of the interface between the arms 110 and the base member 104 or just at a position where the base member 104 and the locking device 108 are fully engaged.

FIG. 2A shows a low profile shoulder assembly 100A that can be assembled from the low profile reverse kit 80A shown in FIG. 1C. The low profile shoulder assembly 82 can include a shoulder assembly 100A and a reverse insert 96A. The reverse insert 96A can be selected from a plurality of such inserts, such as following a determination of which insert provides sufficient but not excessive tension in the soft tissue around the shoulder joint. For example, in one embodiment the low profile reverse kit 80A can include a first reverse insert 96B-1 that has an inferior-superior height that is well suited for patients who have distended or lax soft tissue around the shoulder joint such that it is useful to position the humerus farther from the scapula during the procedure. When first reverse insert 96B-1 is coupled directly with the cylindrical member 908 of the base member 104A a greater spacing is provided between the resection plane and the scapula or between a prominence of the humerus (such as the greater tuberosity) and a landmark of the scapula (such as the acromion). The low profile reverse kit 80A can include a second reverse insert 96B-2 that has an inferior-superior height that is less than that of the first reverse insert 96B-1 and may be well suited for patients who have average soft tissue around the shoulder joint such that it is useful to position the humerus somewhat closer to the scapula during the procedure than would be the case with the first reverse insert 96B-1. When the second reverse insert 96B-2 is coupled directly with the cylindrical member 908 of the base member 104A a spacing is provided between the resection plane and the scapula or between a prominence of the humerus (such as the greater tuberosity) and a landmark of the scapula (such as the acromion) that is less than that provided by the first reverse insert 96B-1. The low profile reverse kit 80A can include a third reverse insert 96B-3 that has an inferior-superior height that is less than that of the second reverse insert 96B-2 and may be well suited for patients who have restrictive or tight soft tissue around the shoulder joint such that it is useful to position the humerus somewhat closer to the scapula during the procedure than would be the case with the second reverse insert 96B-2. When the third reverse insert 96B-3 is coupled directly with the cylindrical member 908 of the base member 104A a spacing is provided between the resection plane and the scapula or between a prominence of the humerus (such as the greater tuberosity) and a landmark of the scapula (such as the acromion) that is less than that provided by the second reverse insert 96B-2.

The low profile reverse kit 80A also can include a reverse insert assembly 96B-4. The assembly 96B-4 is configured to directly couple with the cylindrical member 908 of the lower profile base member 104A. The assembly 96B-4 can include a spacer 909 that is configured to directly couple with the base member 104A, e.g., with an inside surface or wall of the cylindrical member 908 or in the recess 102 if the spacer is provided with a tapered projection similar to the tapered projection 98. A reverse insert 96A is configured to directly couple with the spacer 909. The spacer 909 and the reverse insert 96A can have a combined inferior-superior height comparable to the first reverse insert 96B-1 but can have the advantage of enabling part of the assembly 96B-4 to be of a more durable material than that of the insert 96A. The insert 96A can be made of a polymeric material. The spacer 909 can be made of a metal, e.g., of titanium, stainless steel, or another biocompatible metal. The spacer 909 can be made of the same material as that used to make the base 104A. The spacer 909 allows any of the inserts 96B-1, 96B-2, 96B-3 to be adjusted to create greater space between the articular surface thereof and the resection plane of the humerus such that greater tension can be induced in the soft tissue around the shoulder joint following surgery.

The low profile base member 104A includes many structures in common with the base member 104. The base member 104A can be configured to be coupled with a locking device 108 to enable the base member 104A to retain its position in the humerus when implanted. In addition, the low profile base member 104A includes a submergible portion 900 and an exposed portion 904. The submergible portion 900 can include the helical structure 224. The low profile base member 104A can include a cylindrical member 908. The cylindrical member 908 can be located opposite the helical structure 224, e.g., extending from the submergible portion 900 into and in some cases to the inferior end of the exposed portion 904. In some embodiments the submergible portion 900 and a portion of the cylindrical member 908 closest to the helical structure 224 can be configured similar to the base member 104 such that the same or a similar method of implantation can be used for each of the base member 104 and the low profile base member 104A.

The reverse insert 96A includes an articular portion 912 and a retention portion 916. The articular portion includes a concave surface 920 configured to articulate over a glenosphere 99. FIG. 18B shows that in various advantageous embodiments the cylindrical member 908 and the retention portion are configured to provide for direct coupling or direct connection between the reverse insert 96A and the low profile base member 104A. The reverse insert 96A can be cylindrical. The reverse insert 96A can be symmetrical, e.g., having the same height on an inferior and a superior portion of the reverse insert 96A. For example, the distance from an inferior end 913 of the retention portion 916 to a superior end 914 opposite the retention portion 916 can be the same all the way around an outer periphery 918 of the reverse insert 96A.

FIGS. 1C and 2A shows a shoulder assembly 100A in an exploded view. The shoulder assembly 100A includes the low profile base member 104A and the locking device 108 discussed above. The locking device 108 includes the proximal support 132 and the arms 110. The arms 110 project distally of the proximal support 132. The arms 110 can be positioned in the pathways 300, projecting distally of the exposed portion 904 when the proximal support 132 of the locking device 108 is disposed within the cylindrical member 908 in the exposed portion 904. As such the arms 110 can be disposed through bone in the space between successive portions of the helical structure 224 of the shoulder assembly 100A. The arms 110 can be positioned radially inward of the outer periphery of the helical structure 224 when the locking device 108 is assembled to the low profile base member 104A.

The low profile base member 104A is generally tapered in the direction away from the exposed portion 904 toward the end of the submergible portion 900 opposite the exposed portion 904. In some embodiments, the arms 110 are also tapered, e.g., narrower toward the end opposite the proximal support 132.

The low profile base member 104A can include an inner core 147 which can be the portion of the low profile base member 104A from which the helical structure 224 extend. The inner core 147 can include the cylindrical portion 260. The helical structure 224 surrounds the cylindrical portion 260 and can surround the entirety of the inner core 147. The cylindrical portion 260 extends distally from the exposed portion 904. The cylindrical portion 260 can include disposed therein a tooling interface for connecting to an inserter to move the low profile base member 104A into the surgical field and to cause the exposed portion 904 to be advanced into the humerus H.

The low profile base member 104A has an external surface 924 disposed between the submergible portion 900 and the exposed portion 904. The external surface 924 can include a bone interface portion 926 and the external surface 924 can extend superiorly from the bone interface portion 926 to the superior end of the low profile base member 104A. In some methods discussed further below the low profile base member 104A can be advanced into the cancellous bone of the humerus H until the helical structure 224 is fully submerged in the bone. The low profile base member 104A can be advanced until at least a portion of the low profile base member 104A is at or below the resection surface of the humerus H. The low profile base member 104A can be advanced until a surface within the cylindrical member 908 is at and in some cases partially inferior of the resection surface of the humerus H.

The cylindrical member 908 can include an inferior wall 930 and a raised outer portion 156A. The raised outer portion 156A can include a side wall 932. The side wall 932 can extend to an inferior end of the low profile base member 104A. The inferior wall 930 and the side wall 932 bound a cylindrical space of the low profile base member 104A to which the reverse insert 96A can be secured as discussed further below. The inferior wall 930 can have apertures for accessing the pathways 300, as discussed above. At the boundary of the inferior wall 930 and the side wall 932 one or a plurality of tool interfaces can be provided as shown. The tool interfaces can be used to disengage the spring arm 168 (or other locking device) as discussed above.

Figure 16:
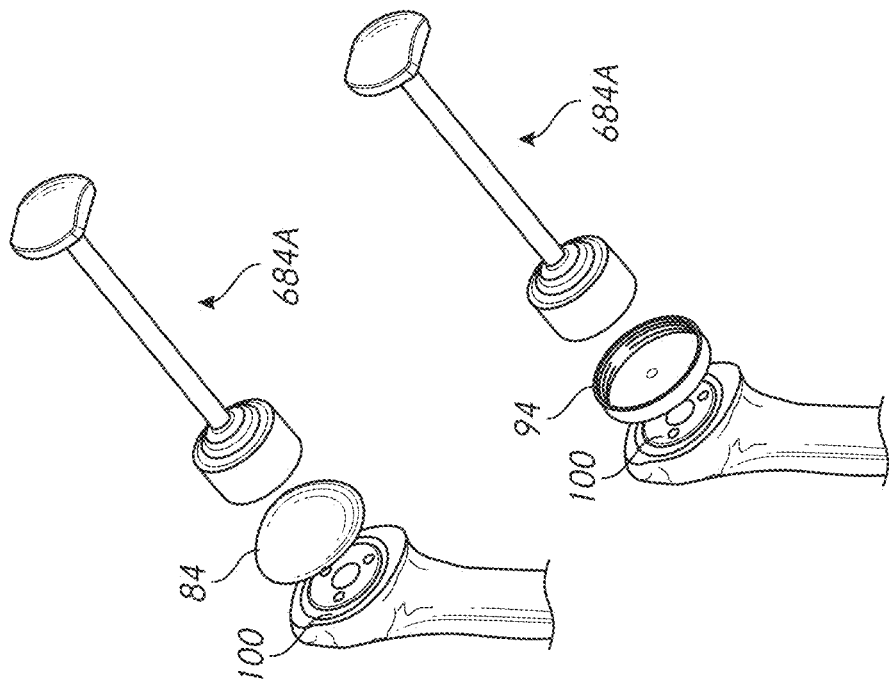
Figure 16A:
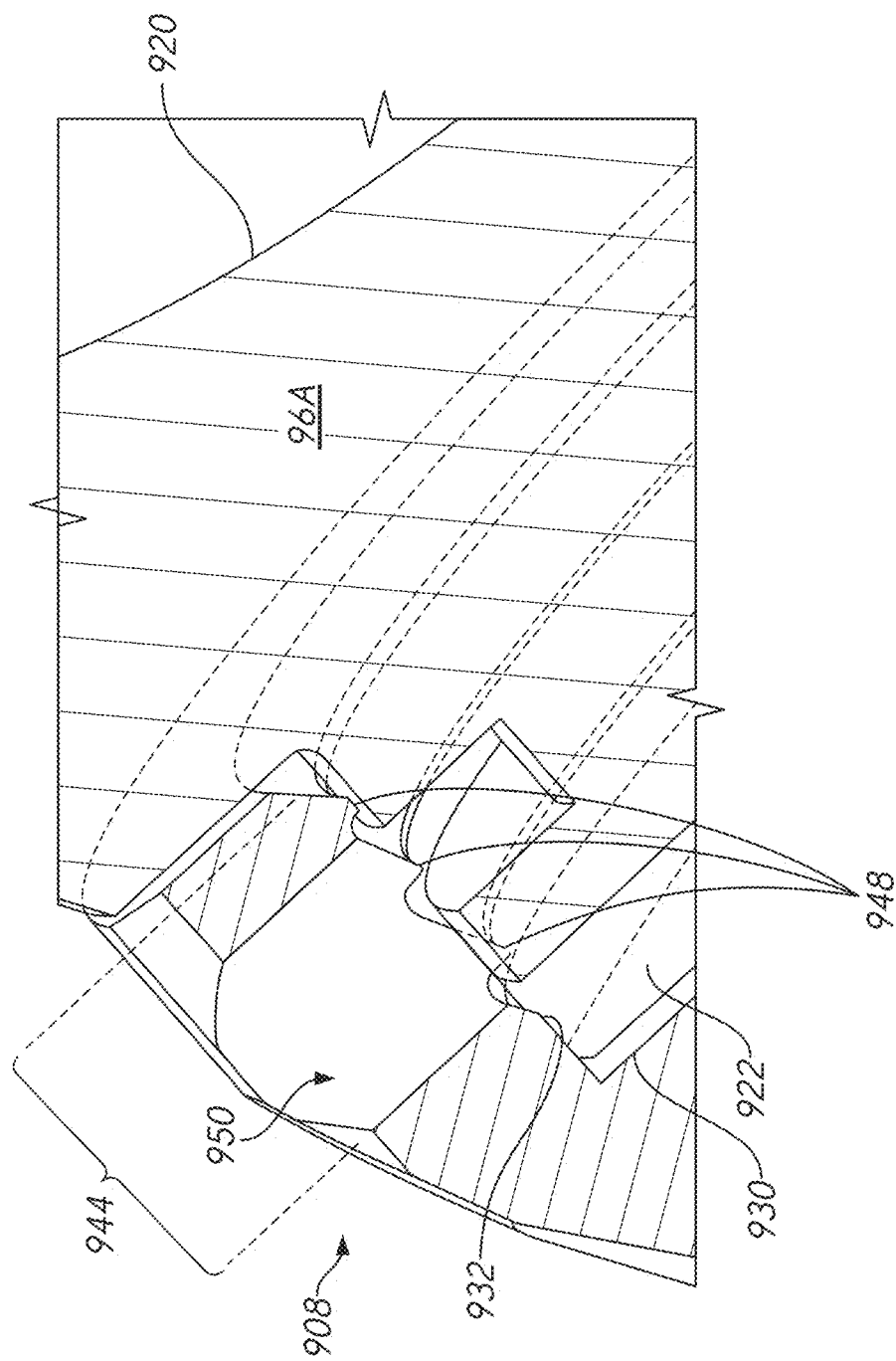
FIG. 16A shows a detail view of a first manner of securing a reverse articular component to a concave member of a low profile base member.
Figure 16B:
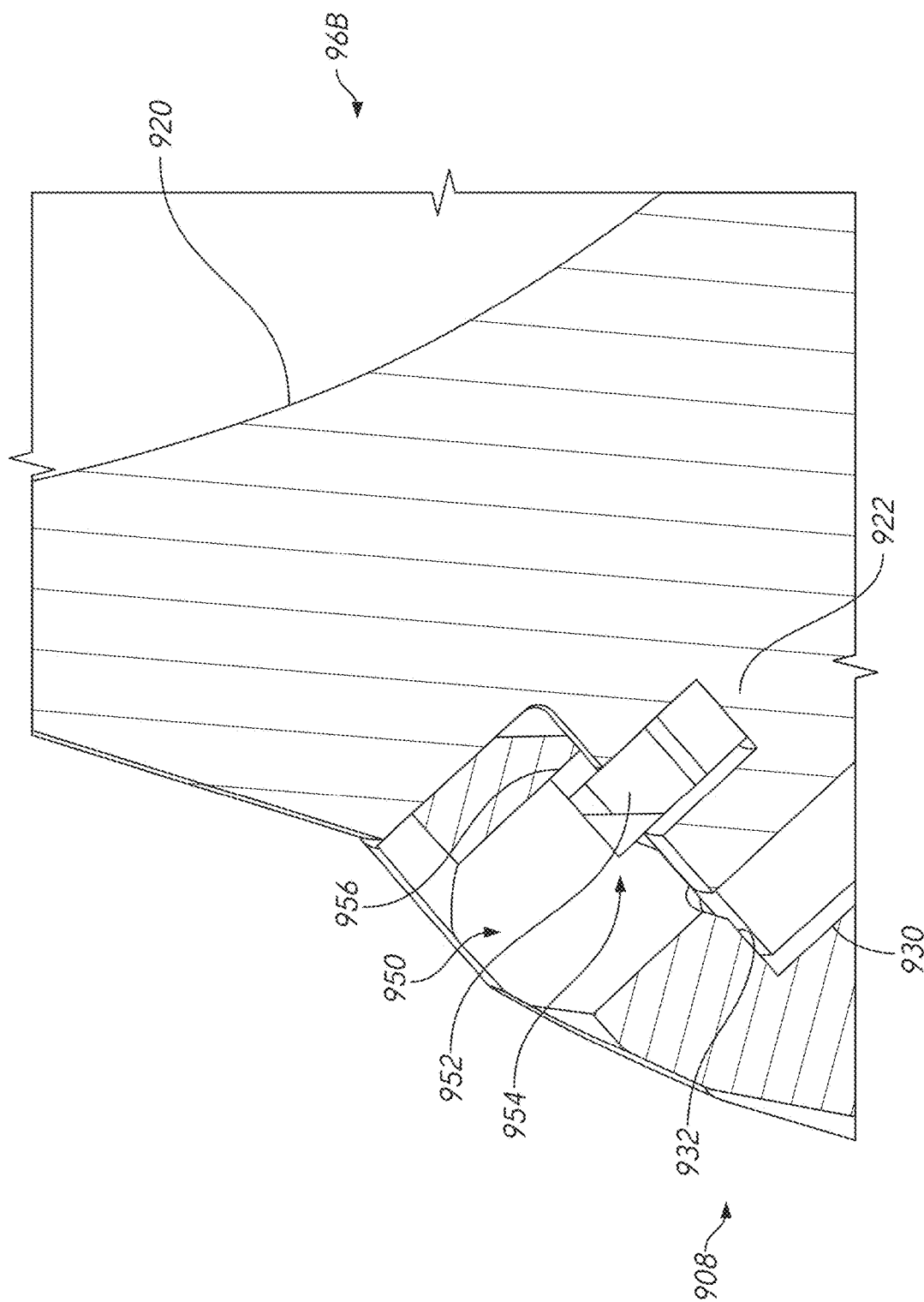
FIG. 16B shows a detail view of a second manner of securing a reverse articular component to a concave member of a low profile base member.

FIGS. 16A and 16B shows variations on how the reverse insert 96A can be secured to the cylindrical member 908. FIG. 16A shows that an interference connection can be provided between the reverse insert 96A and the cylindrical member 908. In one embodiment, one or more ridges 944 can be provided extending radially inwardly from an inner portion of the side wall 932. The ridge 944 can extend to a peak 948 disposed inward of the side wall 932. The reverse insert 96A can have an outer periphery, e.g., an outer radius, that is larger than the dimension defined by the peaks 948. In inserting the reverse insert 96A into the cylindrical member 908 an interference fit can be provided between the reverse insert 96A and the cylindrical member 908 that securely holds the reverse insert 96A in the low profile base member 104A. The cylindrical member 908 can be made of a material that is more rigid than the material used to make the reverse insert 96A. As a result the retention portion 916 of the reverse insert 96A can be compressed during insertion creating a strong connection between the reverse insert 96A and the low profile base member 104A. One or a plurality of opening 950 can be provided in the cylindrical member 908 to allow a tool to be inserted through the cylindrical member 908 into direct contact with the retention portion 916 to disengage the retention portion 916 from the side wall 932 of the cylindrical member 908.

FIG. 16B shows another embodiment in which a C-ring 952 is provided for mechanically and more easily releasably coupling a reverse insert 96B with the low profile base member 104A. The C-ring 952 can be compressible such that upon initial insertion of the reverse insert 96B into the cylindrical member 908 the C-ring 952 is compressed to a smaller diameter. When compressed the reverse insert 96B can slide along the side wall 932 until the reverse insert 96B reaches the inferior wall 930. When the inferior end of the retention portion 916 is at or adjacent to the inferior wall 930 the C-ring 952 expands into an enlarged channel 954 disposed in the side wall 932. When in the enlarged channel 954 the C-ring 952 has superior surface that overlap with an inferior-facing surface 956 of the enlarged channel 954. As such the enlarged C-ring 952 blocks the reverse insert 96B from being removed from the cylindrical member 908. The C-ring 952 can be easily compressed for removal by inserting a tool into the openings 950 as discussed above. In one embodiment there are four openings 950 which can be spaced 90 degrees apart from each other.

In some embodiments structures can be provided to rotationally fix the reverse inserts 96A, 96B within the low profile base member 104A. In some embodiments one or more anti-rotation features 960 are provided to limited, reduce or eliminate rotational motion of the reverse insert 96A, 96B within the low profile base member 104A. The anti-rotation features 960 include a plurality of discrete spaced apart engagement structures that can engage the outer periphery 918 of the reverse insert 96A. The anti-rotation features 960 can include, for example, radial barbs 964 which can be in form of radially projecting and ridges that are aligned with a superior-inferior direction. As such the radial barbs 964 can extend directly into a side surface of the retention portion 916. The radial barbs 964 can be dispersed equally around the side wall 932, e.g., 60 degrees apart from each other. A plurality of radial barbs 964 can be at other positions, e.g., at 30 degrees, 40 degrees or 50 degrees from each other.

II. Method of Application to an End Portion of a Long Bone

FIGS. 8-16 illustrate various techniques for implanting the shoulder assembly 100 in a humerus H. The method illustrates placement in a proximal end of the humerus H, e.g., in the humeral head h.

Figure 8:
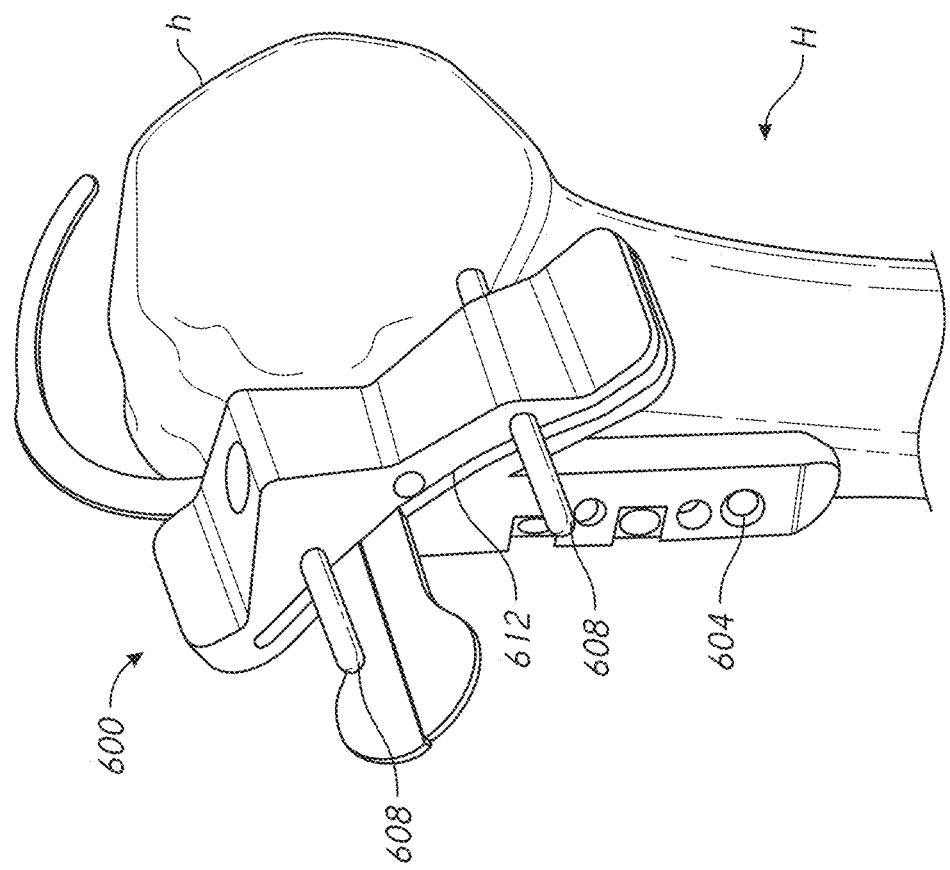
FIGS. 8-16 illustrate various methods for implanting a prosthesis assembly of FIGS. 1-7 into a portion of a bone.
Figure 9:
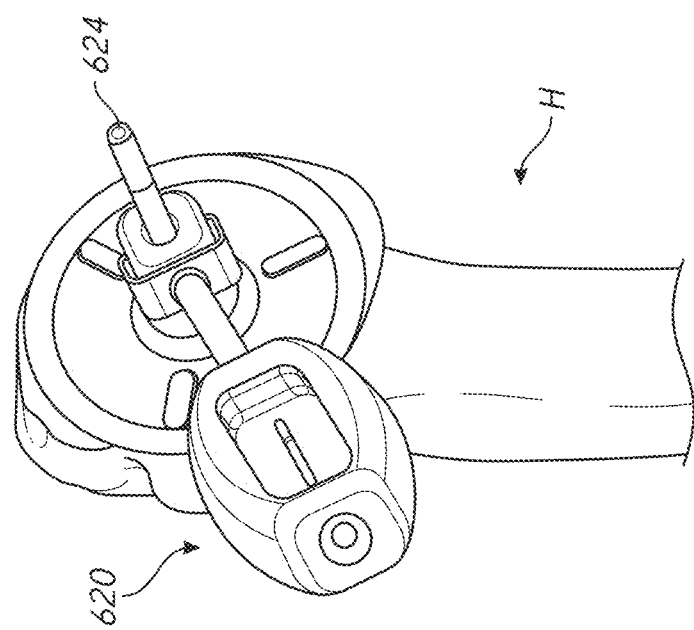

FIG. 8 illustrates an early step of one embodiment of a method including resecting the head h of the humerus H. Prior to resecting the head h of the humerus H a guide 600 is applied to the humerus H. The guide 600 includes structure for mating with the humerus H and the head h, for example, a plate 604 to mate with the humerus H and pins 608 to mate with the head h. The guide 600 also has a slot 612 to guide a saw to cut the humerus H to expose cancellous bone of the head h. FIG. 9 shows that after resecting the head h of the humerus H the size of the head is evaluated with a template 620. To obtain a quick and accurate sizing, a guide pin 624 is first placed in the resected head h. The template 620 is advanced over the guide pin 624 into contact with the resected head. The size of the resected head h is determined from the template 620. The guide 600 can be a reusable guide that is not specific to any particular patients. In other embodiments, the guide 600 is formed with reference to a specific patient. That is, the guide 600 can be formed to mate with the patient, such as by conforming in whole in part on a bone facing side to the shape of the bone as observed or measured using imaging or other devices prior to surgery.

Figure 10:
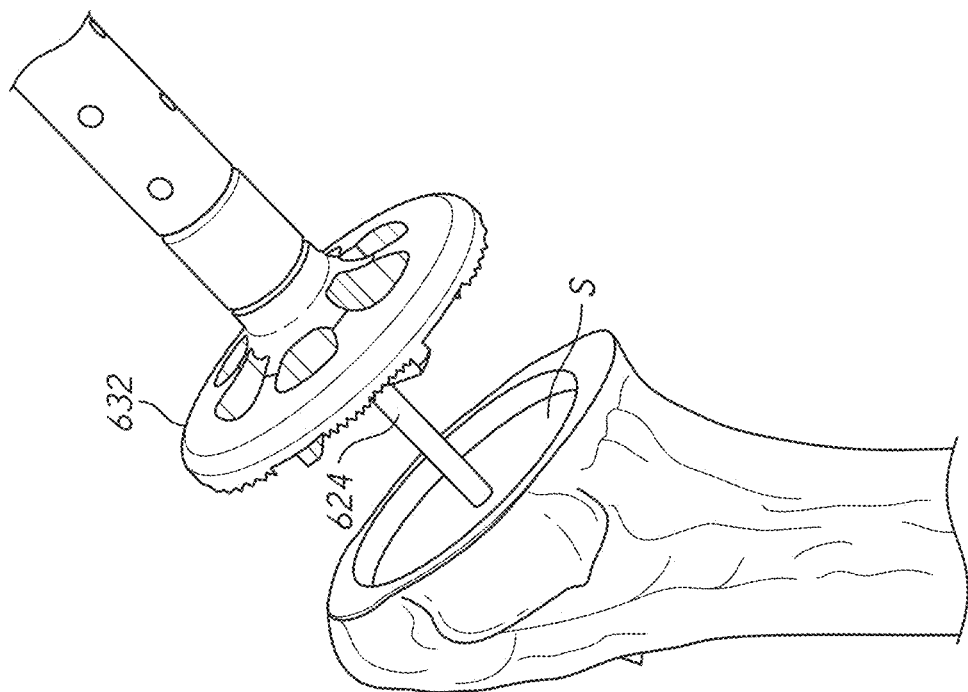

FIG. 10 shows that the resected surface of the head h can be prepared, such as by using a planar or a reamer 632. The reamer 632 also can be guided by the guide pin 624. The reamer 632 can be used to form a recessed surface s to which the assembly 100 will be applied after further preparation.

Figures 11, 12:
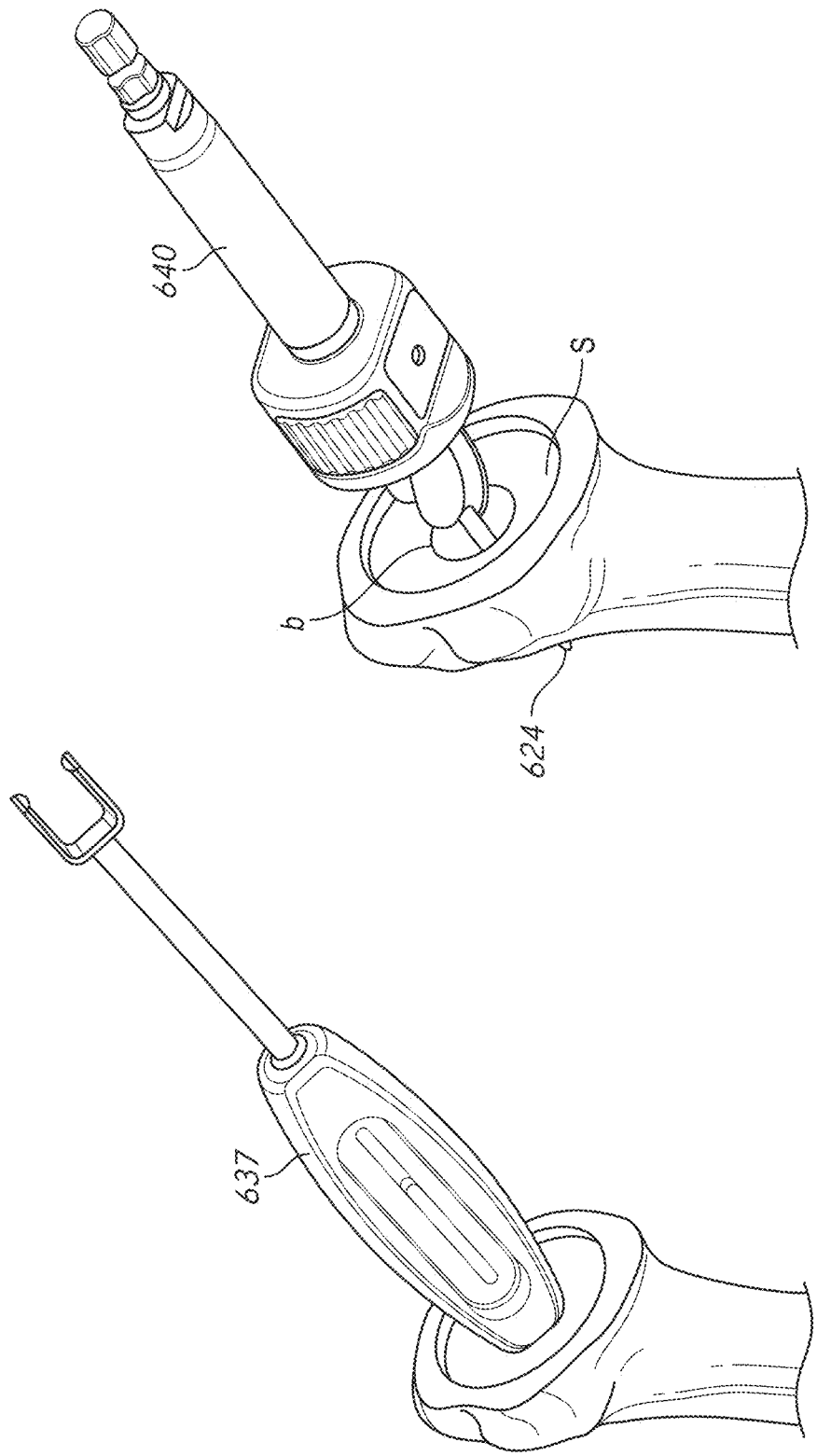

FIG. 11 shows a step of measuring depth of the recessed surface s. The purpose of this step is to provide a secondary confirmation that the assembly 100 will fit into the metaphysis without striking the lateral cortex. While the analysis of FIG. 9 indicates a diameter of base member 104 that could be used, the depth gauge 637 of FIG. 11 provides a depth sizing that confirms a maximum length, e.g., depth, that would fit in the recessed surface S surgeon is instructed to take the smaller of the two sizes determined.

FIG. 12 illustrates that following depth measurement, a bore b is formed in the surface s in initial preparation of the surface s to receive the shoulder assembly 100. The bore b is formed using a drill 640. The drill 640 can be a convention cannulated design configured to be advanced over the guide pin 624. The drill 640 can be configured as a universal drill with a modular stop to obtain variable lengths. The drill 640 can be one of a plurality of drills, each drill of the plurality having a different size as appropriate. In certain methods, the process of forming the bore b and reaming the surface s as discussed above in connection with FIG. 10 can be combined. For example, a drill 640 can have a reaming feature disposed proximally of the bore forming features such that a continuous motion toward the surface formed using the guide 600 can initially form the bore b and subsequently form the surface s. FIG. 13 shows that once the bore b has been formed, the bore b can optionally be tapped to be prepared to receive the base member 104 of the shoulder assembly 100. The tapping process can be achieved by using a helical tap component 648 that is advanced over the guide pin 624. The helical tap 648 can follow the form of the helical structure 224 of the base member 104 such that the base member 104 can be easily advanced into the bore. The helical tap 648 can be secured to a shaft 654 that can be mounted to a motor driven drill or to a hand tool.

Figures 13, 14:
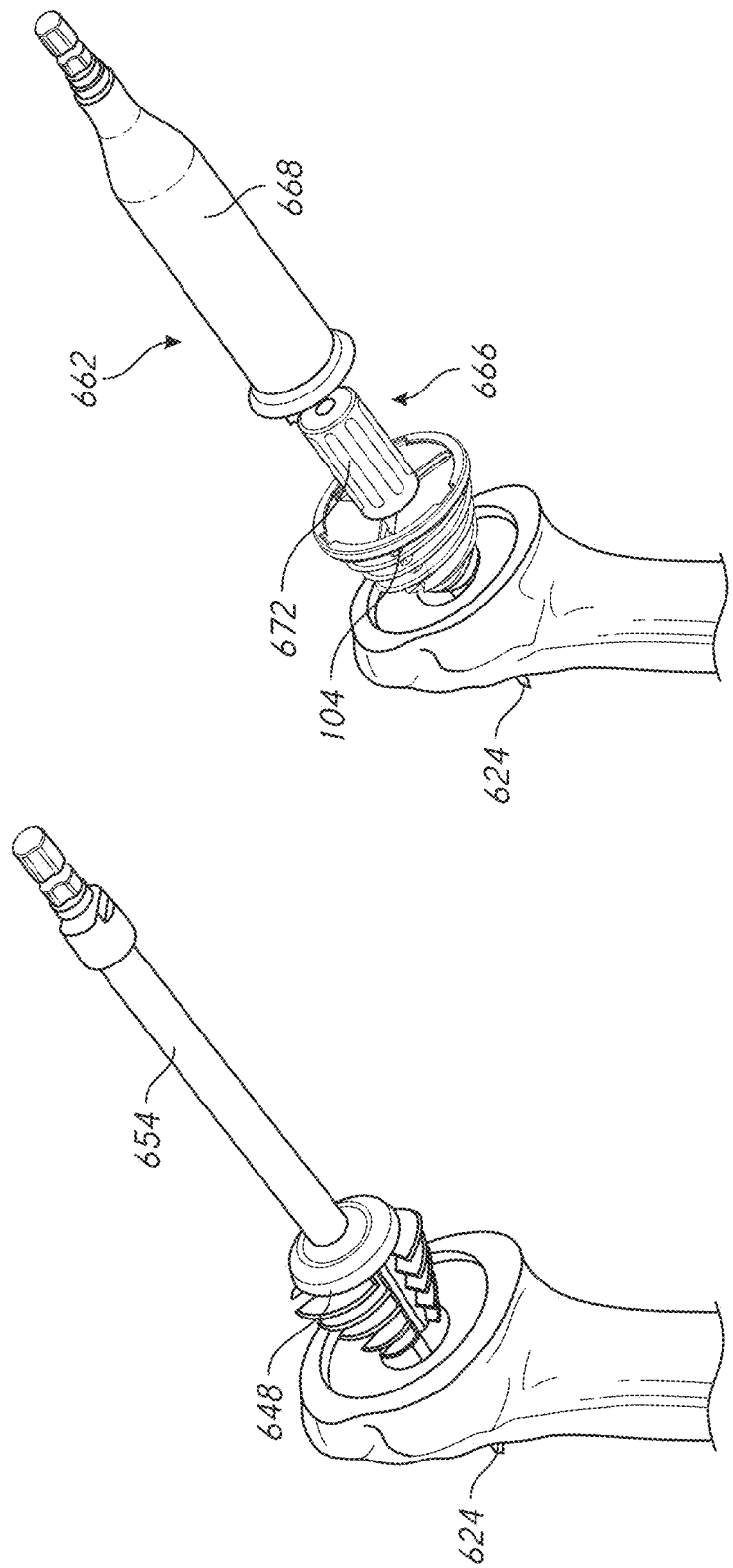
Figure 14A:
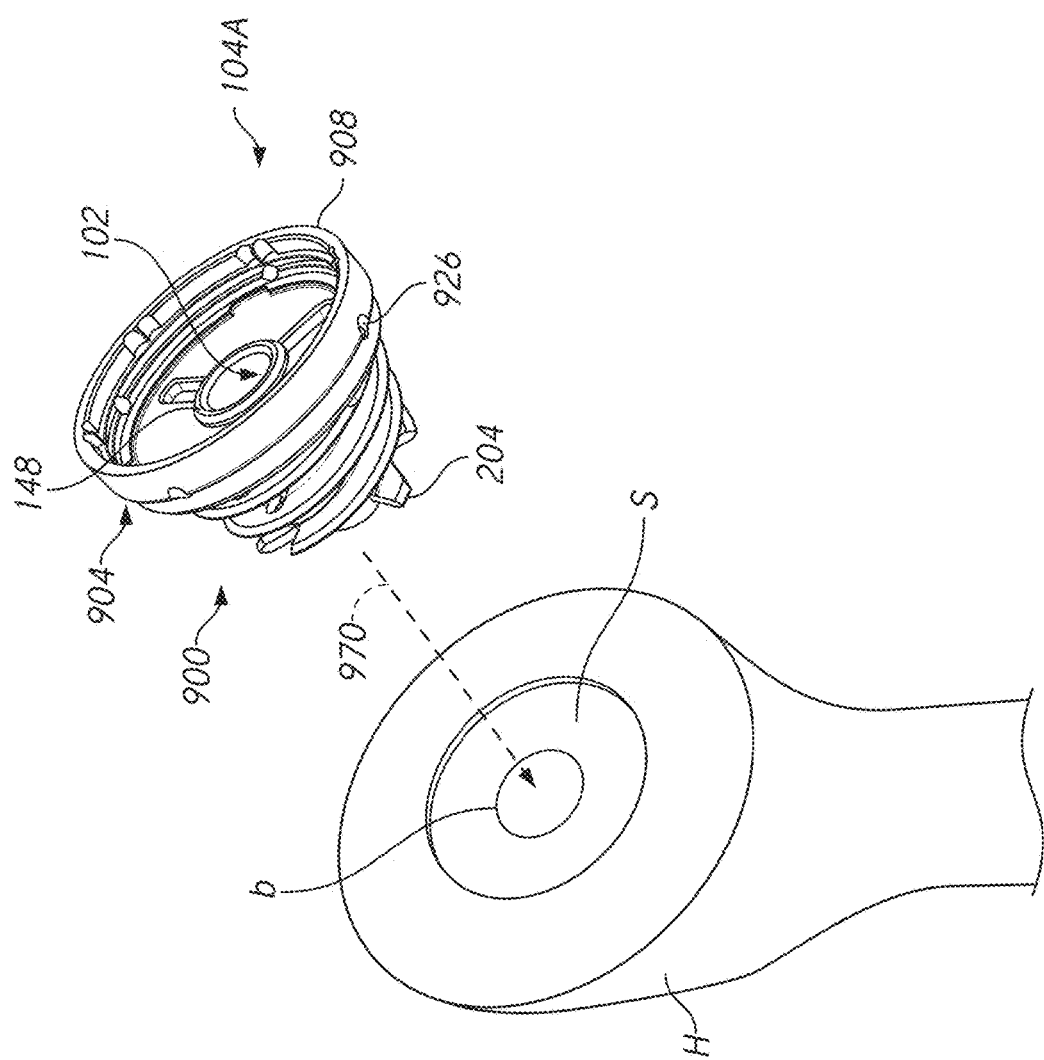

FIG. 14 shows a step of inserting the base member 104. The base member 104 is secured to a distal end of an inerter 662. The inserter 662 has a stem 666 that is threaded at a distal end thereof. The threads of the stem 666 can be mated with the tool interface 272 (see FIG. 7), e.g., with threads of the tool interface. Preferably the stem 666 is enlarged at a mid-section thereof providing at least a shoulder that can mate with the inner raised portion 148 of the base member 104. A separate member 668 of the inserter 662 is advanced over the stem 666 to the tool interface 158, and the force of advancing the base member 104 thus can be applied through the tool interface 272, through the inner raised portion 148, through the apertures 124 or through more than one of these (or other) features of the base member 104. Splines 672 provide for good grip by the surgeon so that the surgeon can easily engage the stem 666 to the tool interface 272. In another variation, a driver with a torqueing device at a proximal end couples at its distal end directly with the tool interface 272, through the inner raised portion 148, through the apertures 124 or through more than one of these (or other) features of the base member 104 to enable more direct transfer of torque to the base member. Preferably inserting the base member 104 into the bone includes placing the outer periphery 154 in the recessed surface s, e.g., at least partially recessed into the resected bone of the humerus H.

FIG. 14A shows that the low profile base member 104A can be advanced into the humerus H in the same manner as the base member 104. Specifically, the surface s can be formed, recessed into the humerus H. The bore b can be formed in the humerus H extending inferiorly from the surface s. The low profile base member 104A can be advanced inferiorly as indicated by the arrow 970. As shown in FIG. 14, the inserter 662 can be coupled with the low profile base member 104A. The stem 666 can be inserted into the recess 102 to abut to an inner raised portion 148 if provided. The stem 666 can provide for handling and initial placement of the first end 204 into the bore b. The stem 666 or the member 668 advanced over the stem 666 can be used to advance the low profile base member 104A into the bore b by engaging the helical structure 224 to the cancellous bone around the bore b. The low profile base member 104A can continue to be advanced until the bone interface portion 926 is disposed in the bone, e.g., in the position shown in FIG. 7A.

Figure 15:
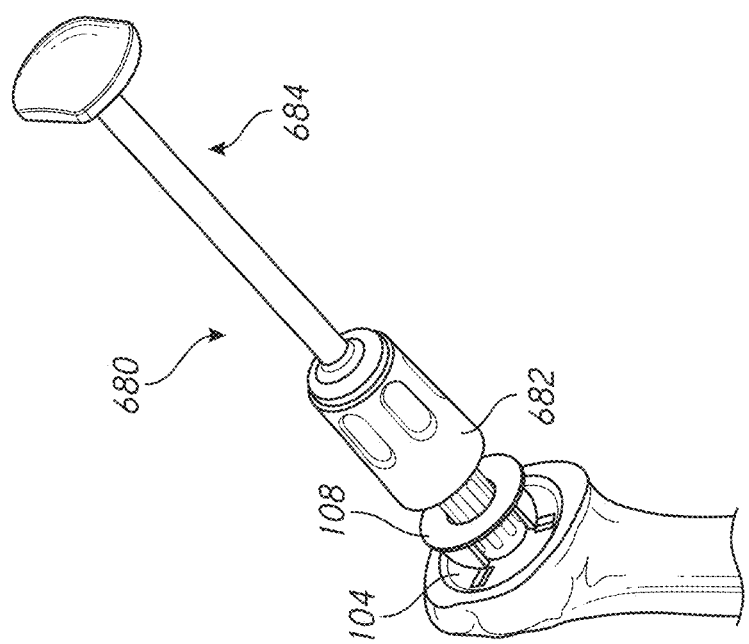

Following placement of the low profile base member 104A in the resected portion of the humerus H the locking device 108 can be advanced in the manner shown in FIG. 15. The locking device 108 can be advanced over the stem 666 into the cylindrical member 908. The locking device 108 can be advanced inferiorly of the side wall 932, for example to a position between anti-rotation features 960 and the inferior wall 930, to a position between the interface 936 and the inferior wall 930, to a position at the base of the side wall 932, or to a position between the side wall 932 and the inferior wall 930.

After the locking device 108 is secured to the low profile base member 104A, an articular insert can be directly coupled with the cylindrical member 908. In other words, following the step of the procedure illustrated in FIG. 15, the reverse insert 96A can be directly coupled with the cylindrical member 908 without the need to couple the tray 94 with the recess 102. The reverse insert 96A can be advanced into the cylindrical member 908 and urged under a force into an interference engagement with the cylindrical member 908. The process can result in some deformation or at least compression of the retention portion 916 within a radially smaller zone of the side wall 932, e.g., within the ridge 944. The reverse insert 96B can be inserted until the C-ring 952 engages a portion of the cylindrical member 908. The cylindrical member 908 can have an angled face that can engage a corresponding angled face of the C-ring 952. Such engagement can cause, by a wedge action, the C-ring 952 to be compressed to allow the reverse insert 96B to further advance until the C-ring 952 is disposed in the enlarged channel 954. When in the enlarged channel 954 the C-ring 952 can engage the inferior-facing surface 956 to secure the reverse insert 96B in the cylindrical member 908 of the low profile base member 104A.

FIG. 15 shows that after the base member 104 has been inserted, the locking device 108 can be inserted. The base member 104 is inserted by a rotation of the member by rotation of the inserter which is directly connected to the base member as discussed above in connection with FIG. 14. The locking device 108 is inserted along the pathway by linear translation, e.g., by a movement along a generally straight axis without rotation. An inserter 680 is provided that has an enlarged head 682 that can be secured to or can just rest upon the proximal face of the annular member 366 of the proximal support 132. The head 682 is then advanced over the splines 672 of the stem 666, with the stem 666 acting as an axial guide. In order to implant the locking device 108 the first end 382 of the arm 110 or arms is aligned with the aperture 124 or apertures if more than one. The arms 110 are radially and circumferentially tapered and the apertures 124 are sized for the wider proximal end of the arms. This configuration helps guide the locking device 108 into the base member 104. The proximal end 684 of the inserter 680 in configured for impacting the locking device 108 into the base member 104.

FIG. 16 shows later steps of a method of implanting an anatomic shoulder prosthesis. After the base member 104 and the locking device 108 are placed, an anatomic articular component 84 can be coupled with the recess 102. The anatomic articular component 84 comprises a convex surface 90, analogous to the natural anatomy. The anatomic articular component 84 is placed with an impactor 684A. Although shown as a separate, dedicated device the insertion and impaction functions illustrated in FIGS. 15 and 16 could be carried out by the same device. For example a contoured face to contact the surface 84 could have a portion configured for inserting the locking device 108 and/or the tray 94.

FIG. 16 shows an alternative step of a method of implanting a reverse shoulder prosthesis. After the base member 104 and the locking device 108 are placed, a reverse articular component 88 can be coupled with the recess 102. In one form, the reverse articular component 88 includes a tray 94. The tray 94 can be coupled with an articular component 96 comprising a concave surface for articulating with a glenoid sphere disposed on a glenoid of a scapula (discussed further below). The tray 94 is placed with an impactor 684A. The reverse shoulder prosthesis including the shoulder assembly 100, the tray 94 and the articular component 96 is shown in FIGS. 18 and 18A. A glenoid sphere 99 mated with a glenoid is shown in FIG. 18A. The shoulder joint provides movement of the patient's arm by articulating the component 96 over the glenoid sphere 99.

In one variation of these methods, assemblies, and kits the locking device 108 is inserted at the same time as some or all of the reverse articular component 88 or at the same time as the anatomic articular component 84. The locking device 108 can be a separate component that is loaded onto an inserter or impacting tool that can be previously loaded with the reverse articular component 88 or the anatomic articular component 84. The locking device 108 can be a separate component that is loaded onto an inserter or impactor with, but relatively moveable to, the reverse articular component 88 or the anatomic articular component 84. The locking device 108 and the reverse articular component 88 can be formed as a monolithic structure that can be loaded together onto an inerter. The locking device 108 and the anatomic articular component 84 can be formed as a monolithic structure that can be loaded together onto an inerter.

III. Advantages and Performance of Embodiments Disclosed Herein

FIGS. 18A and 18B illustrate advantages of the low profile base member 104A and the shoulder assembly 100A that can be formed therefrom. As discussed above, the low profile base member 104A facilitates a low profile shoulder assembly. The result is that the surgeon is given more control over the position of the various components of the shoulder assembly and over the degree of tension in soft tissue around the shoulder joint following the procedure. This has several important benefits. The shoulder assembly 100 has a first profile height $H_1$. The first profile height $H_1$ is a maximum height dimension of the shoulder assembly 100 as measured from the first end 204 to the superior end 97 of the insert 96 coupled with the base member 104. The first profile height $H_1$ can be seen to be much larger than the second profile height H2, which is measured from the first end 204 of the low profile base member 104A to the superior end 914 of the reverse insert 96A. A correspondingly smaller dimension can be provided from the first end of the low profile base member 104A to the inferior portion of the articulation portion 912 that is provided from the first end of the base member 104 to the inferior portion of the articulation portion thereof. As a result the resected humerus can be positioned farther away from the glenoid at the same or lesser soft tissue tension than the shoulder assembly 100 including the base member 104.

Figure 18C:
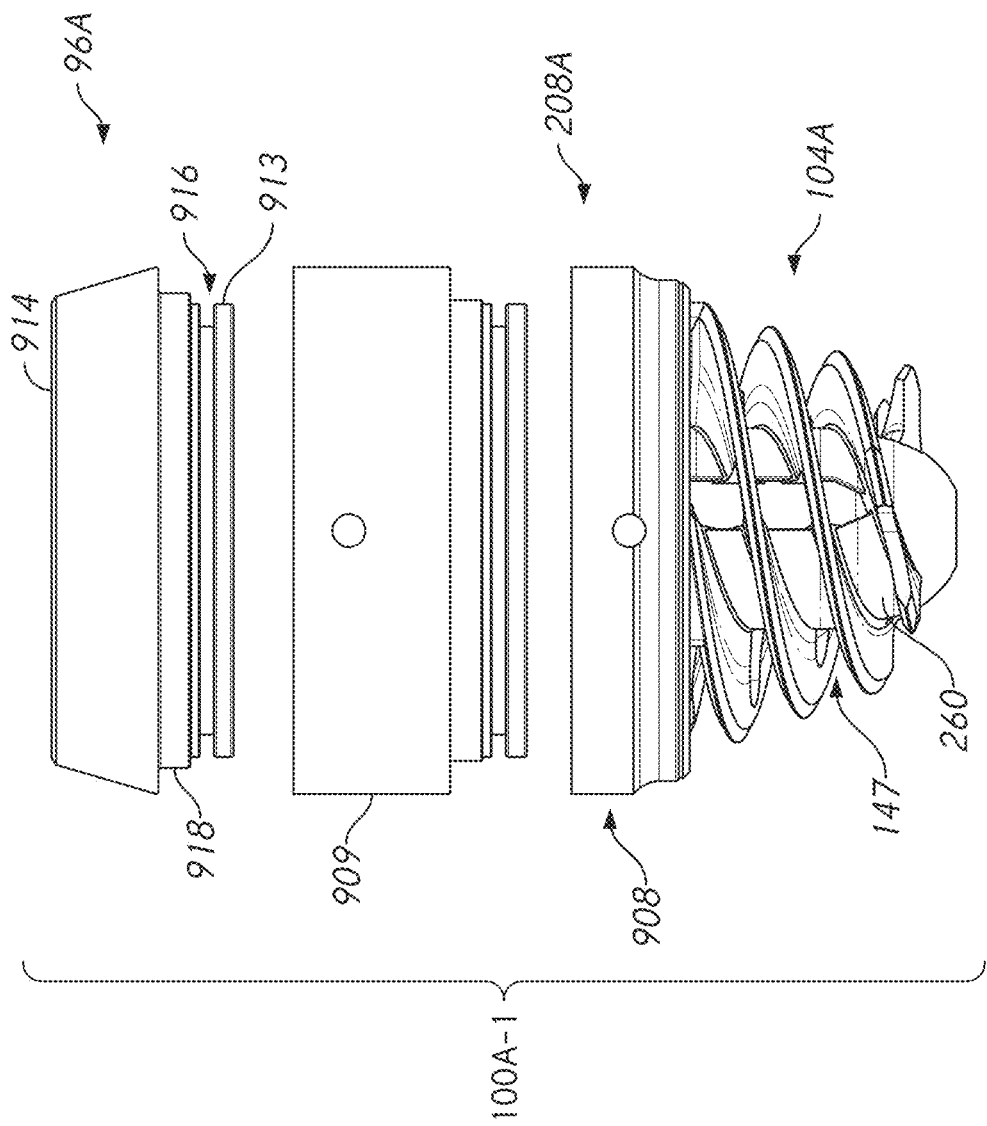
FIG. 18C shows an exploded view of shoulder assembly including a spacer, the shoulder assembly being assembled from the kit of FIG. 1C.

FIG. 18C shows further advantages of a shoulder assembly 100A-1 that can be formed using the spacer 909. As discussed above, the spacer 909 can be provided in a kit with other component discussed herein. For a patient requiring more spacing between the articular surface of a reverse shoulder insert and a resection plane of a humerus a larger insert (such as the first insert 96A-1) can be provided. If more spacing is required, the spacer 909 can be combined with the first insert 96A-1 to further increase the spacing between the articular surface of a reverse shoulder insert and a resection plane of a humerus. By increasing the spacing between the articular surface of a reverse shoulder insert and a resection plane of a humerus soft tissue that are distended or lax can be tensioned following surgery. The shoulder assembly 100A-1 can be provided by initially embedding the submergible portion 904 of the base 104A in the cancellous bone at and inferior of the resection plane. Thereafter, the spacer 909 can be secured in the cylindrical member 908. The spacer 909 can be coupled in any suitable way, such as using the structures illustrated in FIGS. 16A and 16B. The impactor 684A can be used to urge the spacer 909 into a locked configuration within the cylindrical member. In an alternative embodiment not illustrated the spacer 909 can have a tapered stem portion that is adapted to be received in the recess 102 of the base member 104A. After the spacer 909 is secured directly to the cylindrical portion 908 or in the recess 102 the reverse insert 96A is secured to the spacer 909. The spacer 909 can have a cylindrical superior portion within an interior wall having the same configuration as that of the cylindrical portion 908. Thus the reverse insert 96A can be secured to the superior portion of the spacer 909 as illustrated in FIGS. 16A and 16B.

FIGS. 19A and 19B show comparative performance of embodiments disclosed herein with respect to a stemless apparatus that does not have the helical structures disclosed herein nor the locking devices. The graph in FIG. 19A shows average pull out force which is measured by a load opposite of the direction of implanting the base member 104. FIG. 19B shows average lever out force which is measured by applying an off axis load at a known or prescribed fixed distance from a surface at or to which a shoulder assembly similar to the assembly 100 was implanted. The tip out force represents the resistance of the device to tipping out or becoming dislodge from the surface when subject to off axis loading. The forces were observed using a load cell or force transducer. As can be seen, the force of one embodiment is more than four times the force that would dislodge the conventional stemless component. This represents a significant improvement in the retention of the apparatuses disclosed herein compared to conventional stemless design which rely to a large extent on ingrowth for securement which can be sufficient some time after implantation but which can be subject to dislodgement prior to full integration by ingrowth. The inventors expect that the assembly 100A will have performance that is at least as good as that illustrated in FIGS. 19A and 19B.

As used herein, the relative terms "proximal" and "distal" shall be defined from the perspective of the humeral shoulder assembly. Thus, distal refers the direction of the end of the humeral shoulder assembly embedded in the humerus, while proximal refers to the direction of the end of the humeral shoulder assembly facing the glenoid cavity when the assembly is applied to the humerus. Distal refers the direction of the end of the humeral shoulder assembly embedded in the scapula, while proximal refers to the direction of the end of the humeral shoulder assembly facing the humerus when the assembly is applied to the glenoid. In the context of a glenoid component, the distal end is also sometimes referred to as a medial end and the proximal end is sometimes referred to as a lateral end.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A prosthesis assembly comprising:
   a base member having a first end and a second end, the base member comprising:
   a cylindrical member configured to receive and directly couple with a reverse insert;
   a helical structure extending between the first end and the second end; and
   a first pathway accessible from the second end and directed toward the first end through the helical structure and being located adjacent to an inner periphery of the helical structure, the first pathway being generally transverse to the helical structure and extending in a space between successive portions of the helical structure; and
   a locking device comprising a support member and a first arm projecting away from the support member, the first arm configured to be disposed in the first pathway when the support member is disposed adjacent to the second end of the base member;
   wherein the first arm is configured to be disposed through bone in the space between successive portions of the helical structure when the prosthesis assembly is implanted.

2. A shoulder assembly comprising:
   a base member including a submergible portion, an exposed portion, and a cylindrical member extending along the submergible portion, the submergible portion including a helical structure, the cylindrical member extending from the submergible portion to the exposed portion;
   a locking device configured to be inserted between an outer periphery of the helical structure and the cylindrical member to resist rotation of the base member relative to bone; and
   a reverse insert having an articular portion and a retention portion, the articular portion including a concave surface configured to articulate over a glenosphere; wherein
   the cylindrical member and the retention portion provide direct coupling between the reverse insert and the base member, wherein the base member comprises a pathway projecting distally of the exposed portion and through the helical structure adjacent to an inner periphery thereof, the pathway being generally transverse to the helical structure and extending in a space between successive portions of the helical structure, and
   the locking device includes a proximal support and an arm projecting distally from the proximal support, the arm to be located in the pathway projecting distally of the exposed portion when the proximal support is within the exposed portion.

3. The shoulder assembly of claim 2, wherein
   wherein the arm is configured to be located through the bone in the space between successive portions of the helical structure when the shoulder assembly is implanted.

4. The assembly of any one of claim 3, wherein
   the arm includes an inner edge and an outer edge positioned radially outward of the inner edge, and
   the outer edge of the arm is through the helical structure along the first pathway when the locking device is coupled with the base member.

5. The shoulder assembly of claim 4, wherein the outer edge of the arm is positioned radially inward of an outer periphery of the helical structure when the locking device is advanced into the base member.

6. The shoulder assembly of claim 4, wherein the arm further comprises a planar surface extending from the outer edge to the inner edge and from the proximal support to a distal end of the arm.

7. The shoulder assembly of claim 4, wherein the outer edge of the arm is tapered between the proximal support and a location away from the proximal support.

8. The shoulder assembly of claim 3, wherein the arm is configured to be disposed through the bone along the submergible portion.

9. The shoulder assembly of claim 2, wherein the base member further comprises an inner core projecting distally from the exposed portion, the inner core configured to directly couple with a tool for implanting the base member in the bone.

10. The shoulder assembly of claim 9, wherein the inner core is tapered between the exposed portion and an end of the submergible portion opposite the exposed portion.

11. The shoulder assembly of claim 2, wherein the cylindrical member further comprises a sidewall and a ridge extending away from the sidewall to a peak, the peak of the ridge defining an inner dimension of the cylindrical member, the inner dimension of the cylindrical member defined by the peak of the ridge being smaller than an outer periphery of the retention portion of the reverse insert, whereby an interference fit is provided between the protrusion of the retention portion of the reverse insert and the cylindrical member when the reverse insert is engaged with the base member.

12. The shoulder assembly of claim 2, whereby an interference fit is provided between the retention portion of the reverse insert and the cylindrical member when the reverse insert is engaged with the base member.

13. The shoulder assembly of claim 2, wherein a periphery of the cylindrical member is spaced from and surrounds a hole configured to receive a tool for driving the base member into the bone.

14. The shoulder assembly of claim 13, wherein the hole configured to receive the tool at least partially forms an annular space in the cylindrical member configured to receive the retention portion.

15. The shoulder assembly of claim 2, wherein when assembled, the base member and the reverse insert are rotationally fixed.

16. A kit comprising:
 the shoulder assembly of claim 2, wherein the reverse insert comprises a first reverse insert; and
 a second reverse insert having a size different from the first reverse insert.

17. The kit of claim 16, further comprising a spacer configured to directly engage the cylindrical member on an inferior side and to directly engage the first reverse insert or the second reverse insert on a superior side.

* * * * *